US012419586B2

(12) United States Patent
Nematihosseinabadi et al.

(10) Patent No.: US 12,419,586 B2
(45) Date of Patent: Sep. 23, 2025

(54) MULTILAYERED DETERMINATION OF HEALTH EVENTS USING RESOURCE-CONSTRAINED PLATFORMS

(71) Applicant: SAMSUNG ELECTRONICS CO., LTD., Gyeonggi-Do (KR)

(72) Inventors: Ebrahim Nematihosseinabadi, San Jose, CA (US); Shibo Zhang, Evanston, IL (US); Tousif Ahmed, San Jose, CA (US); Md Mahbubur Rahman, San Jose, CA (US); Anh Minh Dinh, San Francisco, CA (US); Nathan Robert Folkman, San Francisco, CA (US); Sean Bornheimer, San Francisco, CA (US); Jun Gao, Menlo Park, CA (US); Jilong Kuang, San Jose, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 741 days.

(21) Appl. No.: 17/840,419

(22) Filed: Jun. 14, 2022

(65) Prior Publication Data
US 2023/0165538 A1    Jun. 1, 2023

Related U.S. Application Data

(60) Provisional application No. 63/283,961, filed on Nov. 29, 2021.

(51) Int. Cl.
*A61B 5/00* (2006.01)
*A61B 5/08* (2006.01)
(Continued)

(52) U.S. Cl.
CPC .......... *A61B 5/7282* (2013.01); *A61B 5/0823* (2013.01); *A61B 5/4803* (2013.01);
(Continued)

(58) Field of Classification Search
CPC ....... A61B 5/113; A61B 5/7282; A61B 5/082; A61B 5/4803; A61B 5/7267;
(Continued)

(56) References Cited

U.S. PATENT DOCUMENTS 8,194,865 B2    6/2012    Goldstein et al.
8,730,048 B2    5/2014    Shen et al.
(Continued)

FOREIGN PATENT DOCUMENTS

KR    20200072030 A    6/2020
WO    2016073965 A1    5/2016
(Continued)

OTHER PUBLICATIONS

WIPO Appln. No. PCT/KR2022/018832, International Search Report and Written Opinion, Mar. 14, 2023, 12 pg.
(Continued)

*Primary Examiner* — Eric F Winakur
*Assistant Examiner* — Hy Khanh Doan
(74) *Attorney, Agent, or Firm* — Kevin T. Cuenot

(57) ABSTRACT

Detecting and identifying a predetermined health event can include detecting a potential occurrence of the predetermined health event for a user by processing in real-time motion signals corresponding to motion of the user. A likelihood that the potential occurrence is an actual occurrence of the predetermined health event can be determined based on template matching of the motion signals. In response to determining that the likelihood exceeds a predetermined threshold, audio signals coinciding in time with the motion of the user can be processed using one or more layers of a multilayered audio event classifier.

20 Claims, 17 Drawing Sheets

(51) Int. Cl.
| | |
|---|---|
| *G10L 21/0208* | (2013.01) |
| *G10L 21/028* | (2013.01) |
| *G10L 25/66* | (2013.01) |
| *G10L 25/78* | (2013.01) |
| *G10L 25/84* | (2013.01) |
| *G16H 40/63* | (2018.01) |
| *G16H 50/20* | (2018.01) |

(52) U.S. Cl.
CPC .......... *A61B 5/7267* (2013.01); *A61B 5/7275* (2013.01); *G10L 21/0208* (2013.01); *G10L 21/028* (2013.01); *G10L 25/66* (2013.01); *G10L 25/84* (2013.01); *G16H 40/63* (2018.01); *G16H 50/20* (2018.01); *G10L 2025/783* (2013.01)

(58) Field of Classification Search
CPC . A61B 5/7275; A61B 5/7264; G10L 21/0208; G10L 21/028; G10L 25/66; G10L 25/84; G10L 2025/783; G16H 40/63; G16H 50/20; G16H 50/80
See application file for complete search history.

(56) References Cited

U.S. PATENT DOCUMENTS

| | | | |
|---|---|---|---|
| 10,229,754 | B2 | 3/2019 | Cronin et al. |
| 11,055,575 | B2 | 7/2021 | Anushiravani et al. |
| 11,109,767 | B2 | 9/2021 | LeBoeuf et al. |
| 11,141,129 | B1 | 10/2021 | Trapero Martin et al. |
| 11,800,996 | B2 * | 10/2023 | Parvaneh ............. G08B 21/043 |
| 11,806,130 | B2 * | 11/2023 | Op Den Buijs ....... G16H 50/20 |
| 2006/0074334 | A1 | 4/2006 | Coyle |
| 2008/0082018 | A1 | 4/2008 | Sackner et al. |
| 2018/0220904 | A1 | 8/2018 | LeBoeuf et al. |
| 2018/0268735 | A1 | 9/2018 | Jihn |
| 2019/0099130 | A1 | 4/2019 | LeBoeuf et al. |
| 2020/0098384 | A1 | 3/2020 | Nematihosseinabadi et al. |
| 2021/0298991 | A1 | 9/2021 | Goldman et al. |
| 2022/0054039 | A1 | 2/2022 | Rahman et al. |

FOREIGN PATENT DOCUMENTS

| | | |
|---|---|---|
| WO | 2017167630 A1 | 10/2017 |
| WO | 2021046237 A1 | 3/2021 |
| WO | 2021222601 A1 | 11/2021 |
| WO | 2023096400 A1 | 6/2023 |

OTHER PUBLICATIONS

Acharya, J. et al., "Deep neural network for respiratory sound classification in wearable devices enabled by patient specific model tuning," IEEE Transactions on Biomedical Circuits and Systems, Mar. 18, 2020, vol. 14, No. 3, pp. 535-44.

"COPD Costs," [online] U.S. Department of Health & Human Services, Centers for Disease Control and Prevention, retrieved from the Internet: <https://www.cdc.gov/copd/infographics/copd-costs.html>, Feb. 21, 2018, 2 pg.

Inserro, A., "CDC Study Puts Economic Burden of Asthma at More Than $80 Billion Per Year," [online] AJMC, The Center for Biosimilars, Jan. 12, 2018, retrieved from the Internet: <https://www.ajmc.com/view/research-suggests-covid-19-vaccines-may-protect-against-pneumonia>, 2 pg.

"What is the economic cost of covid-19?" [online] The Economist Newspaper Limited © 2022, Jan. 9, 2021, retrieved from the Internet: <https://www.economist.com/finance-and-economics/2021/01/09/what-is-the-economic-cost-of-covid-19>, 6 pg.

"Noise Assessment—Noise Descriptors for Environmental Noise," [online] Environmental Protection Department, The Government of the Hong Kong Special Administrative Region, retrieved Apr. 15, 2022, retrieved from the Internet: <https://www.epd.gov.hk/epd/noise_education/web/ENG_EPD_HTML/m2/types_3.html>, 4 pg.

Nematihosseinabadi, E. et al. "Estimation of the Lung Function Using Acoustic Features of the Voluntary Cough," 42nd Annual International Conference of the IEEE Engineering in Medicine & Biology Society (EMBC), IEEE, Jul. 20, 2020 (pp. 4491-4497), Abstract.

Chatterjee, S. et al., "Assessing severity of pulmonary obstruction from respiration phase-based wheeze-sensing using mobile sensors," Proceedings of the 2020 CHI Conference on Human Factors in Computing Systems. Apr. 21, 2020, pp. 1-13.

Nathan, V. et al., "Extraction of voice parameters from continuous running speech for pulmonary disease monitoring," 2019 IEEE International Conference on Bioinformatics and Biomedicine (BIBM). IEEE, 2019, 3 pg., Abstract.

Larson, S. et al., "Validation of an automated cough detection algorithm for tracking recovery of pulmonary tuberculosis patients," (2012): e46229, 10 pg.

Kumar, A. et al., "Estimating Respiratory Rate From Breath Audio Obtained Through Wearable Microphones," arXiv preprint arXiv:2107.14028, In 2021 43rd Annual International Conference of the IEEE Engineering in Medicine & Biology Society (EMBC), pp. 7310-7315.

Nematihosseinabadi, E. et al., "CoughBuddy: Multi-Modal Cough Event Detection Using Earbuds Platform," 2021 IEEE 17th International Conference on Wearable and Implantable Body Sensor Networks (BSN). IEEE, Jul. 27, 2021, pp. 1-4 (IEEE).

Zhang, S. et al., "A Novel Multi-Centroid Template Matching Algorithm and Its Application to Cough Detection," In 2021 43rd Annual International Conference of the IEEE Engineering in Medicine & Biology Society (EMBC) Nov. 1, 2021 (pp. 7598-7604). IEEE. / arXiv preprint arXiv:2109.00630 (2021).

\* cited by examiner

MULTILAYERED DETERMINATION OF HEALTH EVENTS USING RESOURCE-CONSTRAINED PLATFORMS

CROSS-REFERENCE TO RELATED APPLICATIONS

This application claims the benefit of U.S. Provisional Patent Application No. 63/283,961 filed on Nov. 29, 2021, which is incorporated herein by reference in its entirety.

TECHNICAL FIELD

This disclosure relates to sensor-based detection of health events, and more particularly, to determining health events using multiple types of sensors.

BACKGROUND

Various types of health events that an individual may experience can be detected based on observable physiological phenomena. The observable physiological phenomena include sounds corresponding to health conditions and episodes. For example, a cough is an observable reflexive action involving a sudden noisy expulsion of air from an individual's lungs. The cough can indicate an adverse pulmonary event such as a lung infection, chronic obstructive pulmonary disease (COPD), bronchitis, or other pulmonary condition. Similarly, shortness of breath (breathlessness or dyspnea) is often observed in an individual who is experiencing cardiac arrest. An individual's loud snoring and episodic cessation of breathing, for example, may indicate a sleep abnormality such as sleep apnea. Accordingly, various types of pulmonary, cardiac, and other health events experienced by an individual can be detected and identified based on signals generated by electronic sensing devices in response to coughs, wheezing, and other physiological phenomena.

SUMMARY

In an example implementation, a method can include detecting a potential occurrence of a predetermined health event for a user by processing in real-time motion signals corresponding to motion of the user. The method can include determining a likelihood that the potential occurrence is an actual occurrence of the predetermined health event based on template matching of the motion signals. In response to determining that the likelihood exceeds a predetermined threshold, the method can include processing audio signals coinciding in time with the motion of the user using one or more layers of a multilayered audio event classifier.

In another example implementation, a system can include one or more processors configured to initiate operations. The operations can include detecting a potential occurrence of a predetermined health event for a user by processing in real-time motion signals corresponding to motion of the user. The operations can include determining a likelihood that the potential occurrence is an actual occurrence of the predetermined health event based on template matching of the motion signals. In response to determining that the likelihood exceeds a predetermined threshold, the operations can include processing audio signals coinciding in time with the motion of the user using one or more layers of a multilayered audio event classifier.

In yet another example implementation, a computer program product includes one or more computer readable storage media, and program instructions collectively stored on the one or more computer readable storage media. The program instructions are executable by computer hardware to initiate operations. The operations can include detecting a potential occurrence of a predetermined health event for a user by processing in real-time motion signals corresponding to motion of the user. The operations can include determining a likelihood that the potential occurrence is an actual occurrence of the predetermined health event based on template matching of the motion signals. In response to determining that the likelihood exceeds a predetermined threshold, the operations can include processing audio signals coinciding in time with the motion of the user using one or more layers of a multilayered audio event classifier.

This Summary section is provided merely to introduce certain concepts and not to identify any key or essential features of the claimed individual matter. Other features of the inventive arrangements will be apparent from the accompanying drawings and from the following detailed description.

BRIEF DESCRIPTION OF THE DRAWINGS

The inventive arrangements are illustrated by way of example in the accompanying drawings. The drawings, however, should not be construed to be limiting of the inventive arrangements to only the particular implementations shown. Various aspects and advantages will become apparent upon review of the following detailed description and upon reference to the drawings.

DETAILED DESCRIPTION

Figure 1:
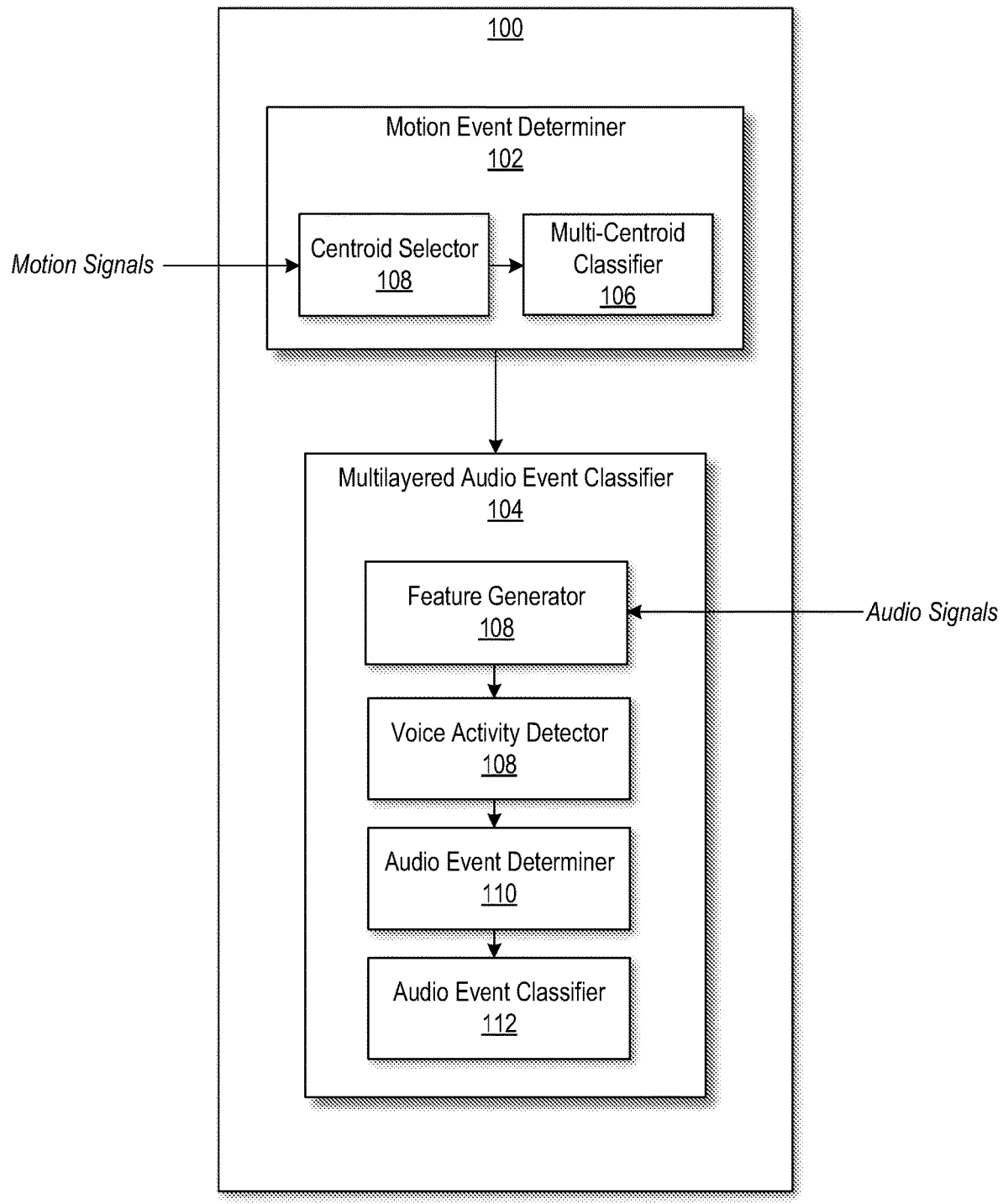
FIG. 1 illustrates an example health event determining system.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to sensor-based detection of health events, and more particularly, to determining health events using multiple types of sensors. As noted above, different types of health events experienced by an individual can be detected and identified based on audio signals generated by electronic sensing devices in response to physiological phenomena. Audio signals generated by a sound transducer in response to an individual's coughing, wheezing, gasping, or similar vocal activity, for example, can detect COPD, asthma attacks, sleep apnea, breathing problems due to Covid-19 or other lung infections, and other adverse pulmonary events.

Notwithstanding various attempts using different detection modalities such as contact microphones and chest-worn sensors, the challenges to providing sensor-based pulmonary monitoring persist. One reason for the too-often poor performance of passive monitoring with many types of portable devices is the frequent presence of events in a real-world environment that result in sensor-generated "false positives." For example, because of similar motion artifacts, a motion-based sensor intended to identify a pulmonary event based on head movements corresponding to an individual's cough may erroneously identify movements generated by the individual's jogging or walking up a flight of stairs as cough-induced head motions. Similarly, an audio-based sensor may mistakenly identify the audio signals generated in response to noises of nearby machinery or a dog's barking as a cough. Assuming a one-second cough duration and ten events mistakenly classified as a cough during an hour (10s/3600s) gives rise to a 99.99 percent likelihood that a sensor-detected pulmonary event is a false positive.

Combining different types of sensors may mitigate the occurrence of some such false positives, but the combining itself raises other challenges, namely having to do with processing overhead and power consumption. Increasing the number of sensors of a device increases both the demands for processing and power for detecting a pulmonary event. Moreover, mitigating false positives, irrespective of the nature of the sensor-generated signal—whether audio, motion, or other—can require complex classification models that consume considerable power. For example, with respect to motion-based detection of a pulmonary event, implementing a conventional template matching algorithm such as a k-nearest neighbor classifier can consume a considerable amount of power. A nearest centroid classifier, for example, may consume less power but at the expense of reduced accuracy.

Likewise, with respect to audio-based detection of pulmonary events, achieving acceptable levels of accuracy with a complex machine learning classifier such as a multilayer neural network or random forest imposes such a high cost in terms of processing and power consumption that it may make implementation with a portable device infeasible. These constraints thus render it difficult if not wholly infeasible to implement in a portable device that might otherwise provide an ideal platform, such as a set of earbuds, a sensor-based system for detecting and identifying pulmonary events with an acceptable level of accuracy.

In accordance with the inventive arrangements described herein, example methods, systems, and computer program products are provided that are capable of detecting and identifying health events (e.g., pulmonary events) with enhanced accuracy while also reducing power consumption. Accordingly, the inventive arrangements described herein are capable of being implemented in various platforms, especially limited-resource platforms such as portable devices and wearables (e.g., earbuds). The inventive arrangements thus can implement accurate health event detection and identification in a device having only limited processing capability and memory, as well as limited power availability (e.g., a battery-powered earbud). The portable device can be used as a stand-alone device or in conjunction with one or more auxiliary devices or platforms (e.g., cloud-based server).

One aspect of certain arrangements described herein is a multilayered sensor fusion architecture implemented in a device (e.g., earbuds) for detecting and identifying certain health events (e.g., cough). As defined herein, "health event" means an audible sound or motion that corresponds to or coincides with an individual's health or a health condition or episode. For example, a physiological event such as the sounds and/or head motions arising from an individual's coughing, wheezing, or gasping are each a health event. The vocal sounds, as well as body motions, associated with coughing, wheezing, and gasping can correspond to a health condition such as COPD or lung infection or can coincide with a health episode such as an asthma attack. Health events encompass more than physiological events such as coughing, however. As defined, a health event can include for example sounds and body motions associated with an individual's eating and drinking—health events that can correspond to conditions such as overeating, excessive fluid intake, or lack thereof. Such health events can be part of the nutritional monitoring of a user who, for example, may need to limit calorie intake. Likewise, body movements and sounds such as snoring, wheezing, and gasping can be monitored to evaluate the pattern and quality of an individual's sleep, which itself is an important health event. Sounds and body movements associated with weeping and/or agitated vocalizations are health events that can be significant indicators of the individual's mental health.

The multilayered sensor fusion architecture balances the trade-off between the sensitivity necessary for detecting a possible health event and the specificity required for confirming the occurrence and identifying the specific type of health event. The trade-off is achieved by dividing a complex classification task into multiple stages. The architecture enhances the accuracy of detection and identification of the health event while also reducing the amount of power needed to accurately make the detection and identification. The achievement of an efficient trade-off between classification accuracy and power consumption makes it possible to implement the inventive arrangements in virtually any portable device equipped with a sound transducer (e.g., microphone) and one or more motion sensors (e.g., inertial measurement unit (IMU)). Thus, the inventive arrangements are well-suited for implementation in wearable devices, including earbuds, smartwatches, smart glasses, mixed-reality headsets, and the like. When implemented in a device intended to be multifunctional, the accuracy-power trade-off of the inventive arrangements enables the device to passively monitor for health events with heightened accuracy without a consumption of power that would impede the device's performing other functions, such handling wireless calls, facilitating game playing, and/or playing music, for example.

In certain arrangements disclosed herein, a low-powered motion classifier operatively couples with a more complex, multilayered audio event classifier. The motion classifier processes sensor-generated motion signals generated in response to a user's body movements. Based on the motion signals, the motion classifier identifies a possible health event of the user. The motion classifier consumes relatively little power. The more complex multilayered audio event classifier determines whether the health event occurred and identifies the type based on audio signals linked to the motion signals. The multilayered audio event classifier consumes an increasing amount of power at each successive layer. Each successive layer is only invoked, however, in response to the preceding layer's determining from the nature of a signal processed that it is likely that a health event occurred. A signal is processed and passed from one layer of the multilayered audio event classifier to the next only on condition that the signal more likely corresponds to a health event. Otherwise, the signal is discarded.

In certain arrangements, the multiples layers of the multilayered audio event classifier include a voice activity detection layer, an audio event detection layer, and audio event classification layer. Voice activity includes coughing, wheezing, throat clearing, and other non-speech sounds, as well as human speech. Only if audio features corresponding to voice activity are detected at the voice activity detection layer are the audio signals conveyed to the audio event detection layer. Only if sharp sounds—sounds (e.g., coughing, wheezing, throat clearing) other than human speech—are detected at the audio event detection layer are the audio signals corresponding thereto conveyed to the audio event classification layer. Thus, an audio signal only reaches the final layer if it has already been determined to contain features that likely correspond to a health event. The classification at the final layer of the multilayered classifier confirms the occurrence of the health event and identifies the type. Accordingly, a succeeding layer's operation is invoked only if the added energy expenditure is likely to lead to the detection and identification of a health event. Otherwise, energy is further conserved by curtailing audio signal processing at the point where there is not a likelihood of determining a health event.

An aspect of the low-powered motion classifier is a sensitivity-skewness whereby the motion classifier is very likely to detect motions that may correspond to a potential occurrence of a predetermined health event while consuming only a limited amount of power. In certain arrangements, the motion classifier classifies motion signals generated by a motion sensor based on a template matching. The template matching can identify motion signals indicating a health event by identifying a match between the signals' "signature," or pattern, with one known to correspond to a specific health event. Template matching not only performs well for classifying motion signals but consumes less power than more complex machine learning models. The template matching can be performed using the novel, self-tuning multi-centroid classifier disclosed herein.

An aspect of the multilayered audio event classifier is a specificity-skewness whereby each of multiple layers provides greater classification specificity to increase accuracy. Each successive layer, given its greater complexity, consumes a greater amount of power but is only invoked in response to a determination at a preceding layer. The more complex classification models, though consuming more power, are capable of processing only the selected portions, e.g., critical portions, of any signal as necessary to make a signal classification. Each model is relieved of the burden of processing any non-critical portions. This further reduces power consumption.

Thus, the arrangements disclosed herein provide classification accuracy but at a reduced cost in terms of power consumption. If at any preceding layer, no potential event is identified, the one or more succeeding layers remain dormant, thereby conserving power. Thus, the inventive arrangements can be implemented more readily in portable devices, including wearable devices such as earbuds, smartwatches, smart glasses, mixed-reality headsets, and the like. Moreover, if implemented in a wearable device, the arrangement can be calibrated to the orientation of the specific user and/or to mitigate manufacturing process variation that might affect classification accuracy.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

Referring initially to FIG. 1, an example health event determining system (system) 100 is depicted. System 100 illustratively includes motion event determiner 102 and multilayered audio event classifier 104. Operatively, motion event determiner 102 detects a potential occurrence of a predetermined health event of a user. Motion event determiner 102 detects the potential occurrence through the real-time processing of motion signals that are generated by one or more motion sensors in response to movement of the user. Motion event determiner 102 determines a likelihood that the potential occurrence is an actual occurrence of the predetermined health event. The determination is based on template matching of the motion signals. In certain arrangements, motion event determiner 102 performs the template matching using multi-centroid classifier 106 described below, a novel, self-tuning classifier. Accordingly, in certain arrangements, motion event determiner 102 comprises multi-centroid classifier 106 and centroid selector 108, also described below. In other arrangements, other types of template matching can be performed by motion event determiner 102. Thus, using multi-centroid classifier 106 or other template matching process, motion event determiner 102 can determine whether the potential occurrence is likely an actual occurrence of a predetermined health event. The likelihood can be a quantitative determination having a predetermined confidence level (e.g., 90 percent, 95 percent).

In response to the determining that the potential occurrence of the predetermined health event is likely an actual occurrence, motion event determiner 102 invokes audio signal processing by multilayered audio event classifier 104. The audio signals processed by multilayered audio event classifier 104 coincide (identically or approximately) in time with the motion of the user corresponding to the likely predetermined health event. Multilayered audio event classifier 104, in certain arrangements described below, comprises feature generator 110, voice activity detector 112, audio event determiner 114, and audio event classifier 116. Using a machine learning classification model, multilayered audio event classifier 104 identifies the predetermined health event based on a classification of select features of the processed audio signal.

Figure 15:
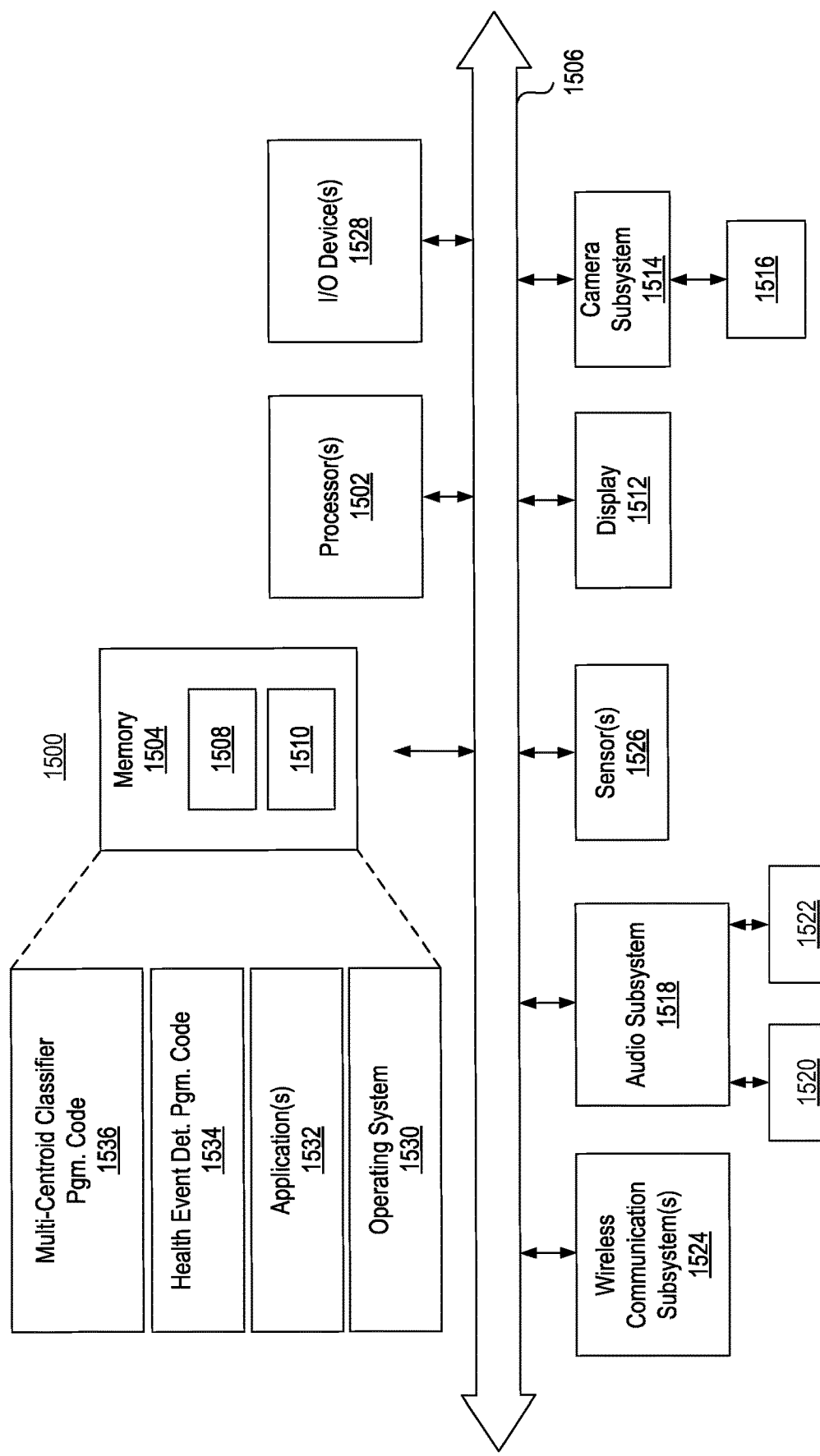
FIG. 15 illustrates an example electronic device used in implementing the system of FIG. 1.

System 100, in various arrangements, can be implemented in hardware (e.g., dedicated hardwired circuitry), software (e.g., program code executed by one or more processors), or a combination thereof. For example, system 100 in certain embodiments is implemented in a device such as device 1500 (FIG. 15). Accordingly, in certain arrangements, system 100 comprises program code that is electronically stored in a memory, such as memory 1504, and executes on one or more processors, such as processor(s) 1502 of device 1500 (FIG. 15). The device can include an audio transducer (e.g., microphone) and one or more motion sensors (e.g., multi-axis IMU) embedded therein.

In some arrangements, system 100 is implemented in a device operates as stand-alone device. In other arrangements, different elements of system 100 are implemented in different devices. For example, motion event determiner 102 can be implemented in a device (e.g., earbuds) that operates in conjunction with one or more operatively coupled auxiliary devices (e.g., smartphone, cloud-based server) that implement multilayered audio event classifier 104. In certain arrangements, motion event determiner 102's motion signal processing is performed with one device, and multilayered audio event classifier 104's audio processing is performed in one or more other devices that provide added processing capabilities. Accordingly, signals captured by motion and audio sensors of a wearable device (e.g., earbuds, smart glasses), for example, can undergo signal processing by a companion device (e.g., smartphone, smartwatch, cloud-based server) that operatively couples with the wearable device and has more robust processing capabilities.

Figure 2:
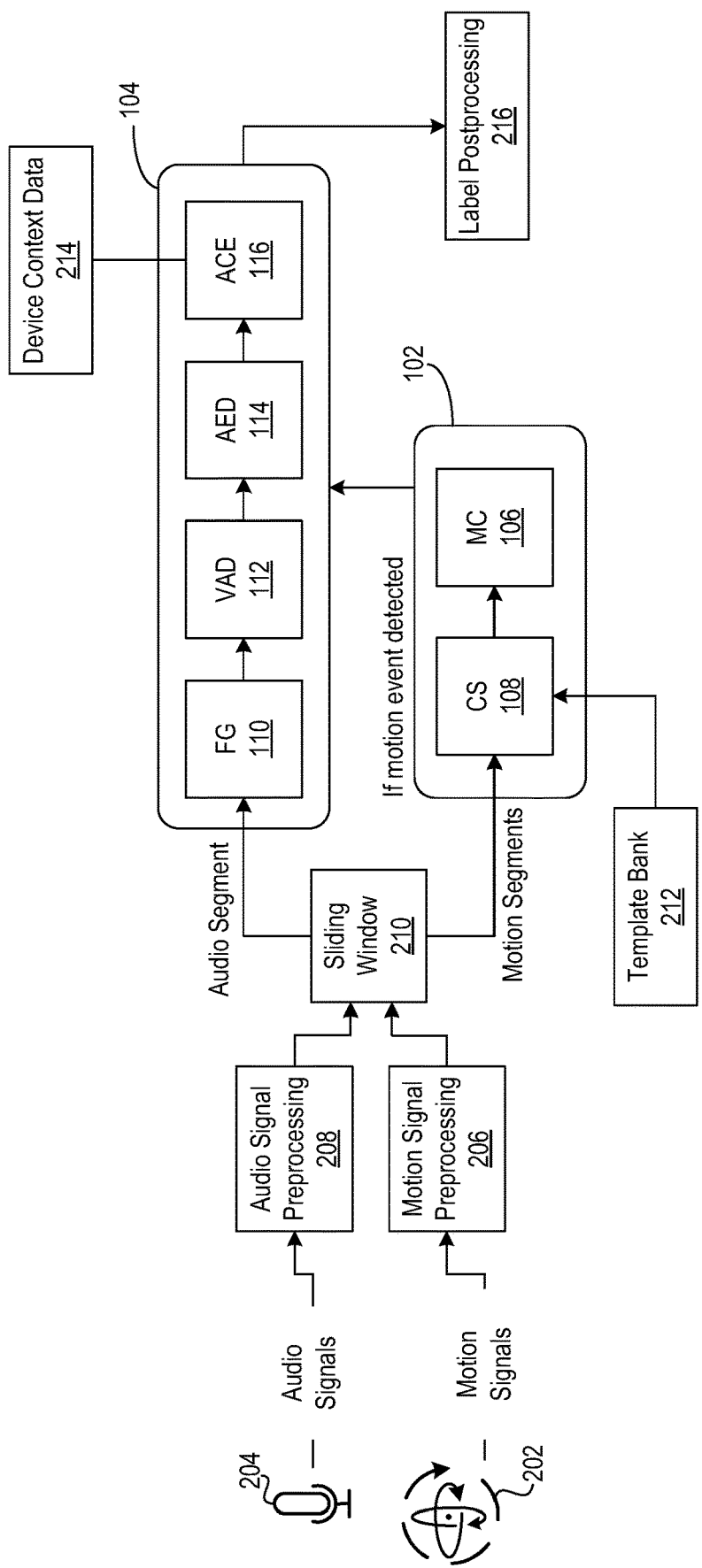
FIG. 2 illustrates certain operative aspects of the system of FIG. 1.
Figure 3:
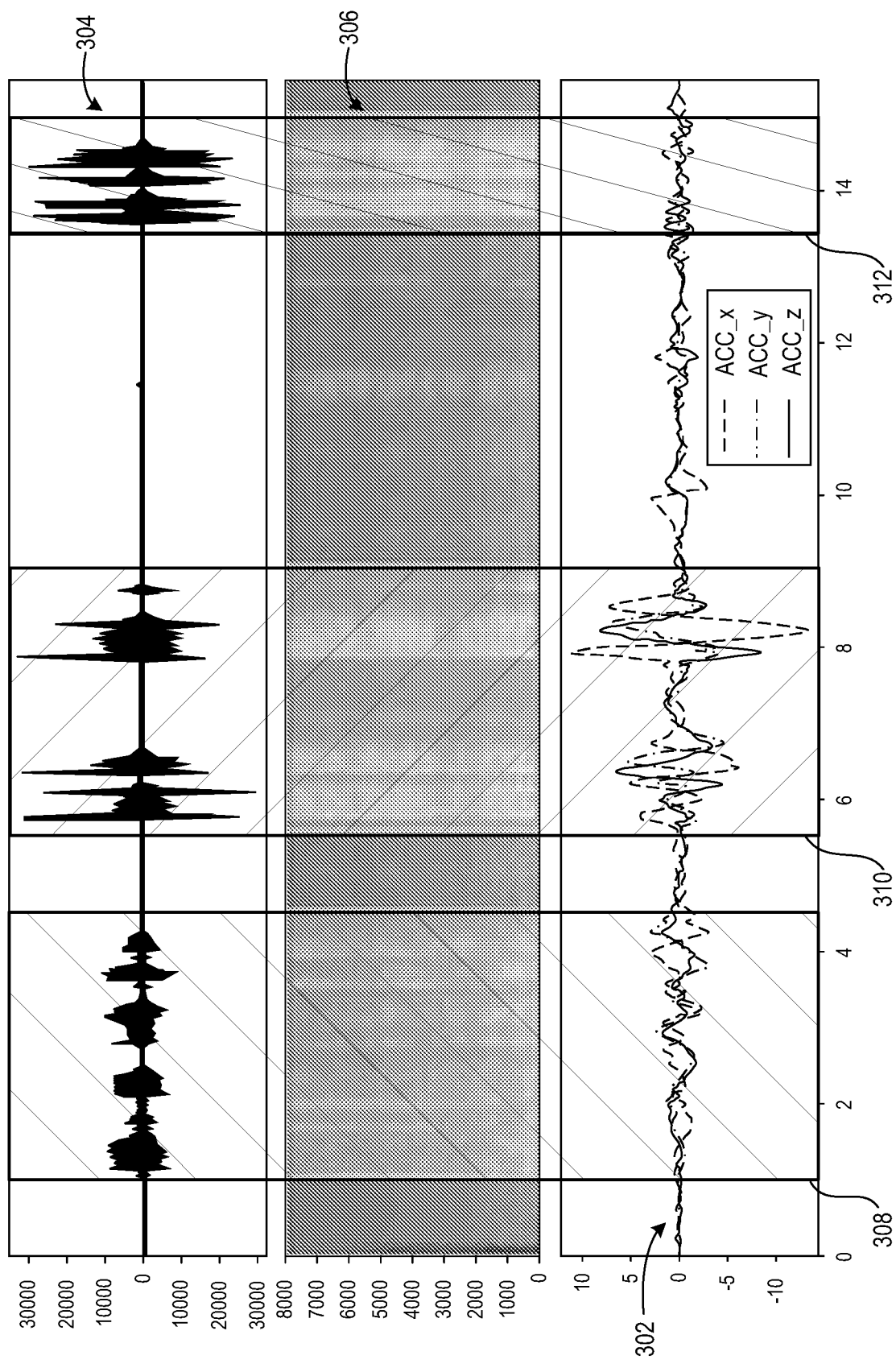
FIG. 3 illustrates example signal waveforms and spectrograms analyzed by the system of FIG. 1.

Referring additionally to FIG. 2, certain operative aspects 200 of system 100 are illustrated in accordance with certain arrangements. Illustratively, the device in which system 100 is implemented includes motion sensor 202 (e.g., multi-axis IMU) and audio transducer 204 (e.g., microphone). Motion sensor 202 generates motion signals in response to user movement. Audio transducer 204 captures audible sounds that coincide in time with or closely correspond in time with the user movements. The motion signals generated by motion sensor 202 in response to user movement can illustratively undergo motion signal preprocessing 206. Motion signal preprocessing 206 can include smoothing, high-pass filtering, and normalization of the motion signals. The audio signals generated from sounds captured by audio transducer 204 can illustratively undergo audio signal preprocessing 208. Audio signal preprocessing 208 can include smoothing, high-pass filtering, and normalization of the audio signals Sliding window 210 performs a time alignment that links the motion signals to corresponding audio signals that coincide in time or closely correspond in time to the motion signals. FIG. 3 illustrates example processed motion signals 302 linked to example processed audio signals 304, and corresponding spectrogram 306. Linked segments 308 correspond to user speech. Linked segments 310 correspond to user coughing. Linked segments 312 correspond to user throat clearing.

Referring again to FIGS. 1 and 2, motion event determiner 102 performs a sensitivity-skewed motion event determination that can identify, based on template matching, whether a segment of the motion signals likely corresponds to a predetermined health event. Motion event determiner 102 determines that the motion event likely corresponds to a predetermined health event by identifying a match between a signature, or pattern, of the motion signal segment and that of a template that corresponds to the predetermined health event. If there is a match, then motion determiner 102 conveys the audio event to multilayered audio event classifier 104. Motion event determiner 102 can identify different potential health events, the identifying based on matching an audio signature with one of multiple motion signatures corresponding to the different potential health events. Templates corresponding to predetermined health events can be selected from electronically stored template bank 212. As described below, if the template matching is performed using multi-centroid clustering 106, the templates are selected by centroid selector 108.

Figure 4:
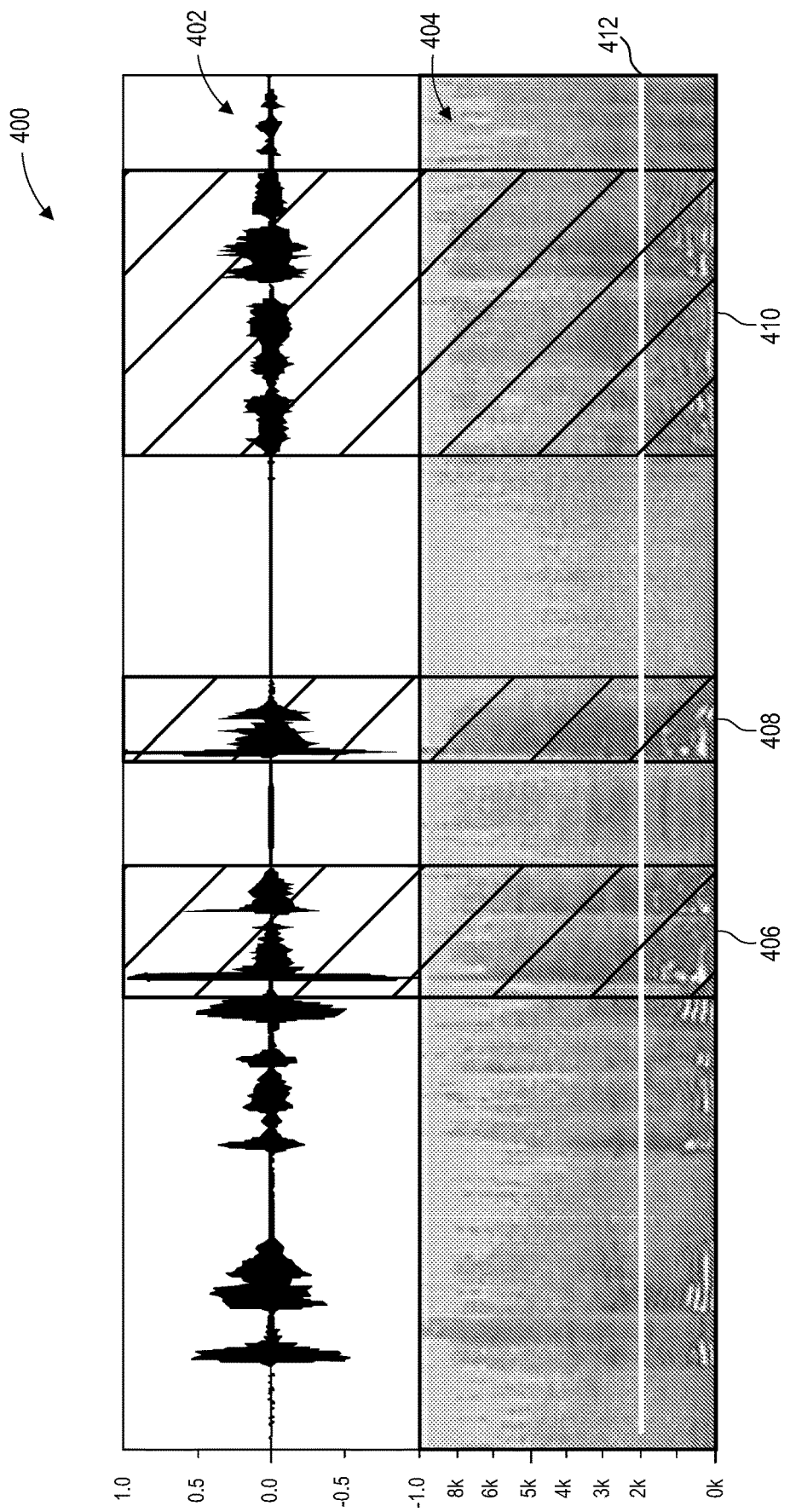
FIG. 4 illustrates example signal waveforms and spectrograms analyzed by the system of FIG. 1.

In response to detecting a motion signature linked to a health event based on template matching, motion event determiner 102 invokes action by multilayered audio event classifier 104, thus triggering an audio processing pipeline. Feature generator 110 of multilayered audio event classifier 104 generates relevant acoustic features from the audio segments linked to the motion detected by motion event determiner 104. The relevant acoustic features can include temporal features such as mean, standard deviation, root mean square (RMS) energy, and zero crossing rate (ZCR), for example. The relevant acoustic features can include spectral features, including mel-frequency cepstral coefficients (MFCCs), spectrograms, spectral density, mel-spectrograms, amplitude envelope, spectral centroids, band energy ratio, and spectral bandwidth, for example. Voice activity detector 110 performs an energy thresholding activity detection that passes all voice activities contained within the audio signals and removes non-voice activities. Voice activities comprise not only human speech but sounds such as throat clearing, coughing, sneezing, wheezing, chewing, swallowing, and other sounds. FIG. 4 illustrates example processed audio signals 402 and spectrograph 404. Segments 406 and 408 correspond to coughs, and segment 410 corresponds to ordinary speech. Segments 406, 408, and 410 comprise voice activities that exceed energy threshold 412, and thus are passed to audio event determiner 114 by voice activity detector 112.

Audio event determiner 114 separates sharp sound events such as coughing from non-sharp events such as ordinary speech. Audio event determiner 114 is invoked only in response to voice activity detector 112 detecting voice activity. Only if audio event determiner 114 detects sharp sound events is audio event classifier 116—the last layer of multilayered audio event classifier 104 and likely the greatest consumer of device power—invoked.

Audio event classifier 116 is capable of classifying the sharp sound events received from audio event determiner 114. The classification by audio event classifier 116 determines the type of health event that a sharp sound event corresponds to. Audio event classifier 116 uses a classifier model to identify the health event. Label postprocessing 216 affixes an electronic label to the sharp sound event. The label identifies the audio signals whose features correspond to the sharp event and identifies the type of health event (e.g., cough, wheeze, gasp). System 100 by labeling the sound event thus outputs an identification of a health event in response to the inputs comprising motion signals and audio signals. The labeled audio segment identified as likely corresponding to a specific health event can be further processed for diagnostic and/or treatment purposes. The diagnosis can be made and/or treatment selected based on the detection and identification of the health event corresponding to the processed motion and audio signals. Some examples of diagnosis and treatment corresponding to pulmonary conditions and episodes are disclosed below.

The classifier model implemented by audio event classifier 116 to identify a health event can be a deep learning neural network, random forest, support vector machine (SVM), or other machine learning model. The particular machine learning model can vary in complexity. Accordingly, the selection of the model used by audio event classifier 116 can affect system 100's power consumption. As described more fully below, optional model selector 214 can be used to select the machine learning model that is used. Model selector 214 optionally selects a model based on the resources available to system 100 from the device in which system 100 is implemented. The device's resources available to system 100 can include, for example, resources such as processor and memory capabilities and resources such as remaining battery life.

The machine learning model used by audio event classifier 116 can be trained through supervised machine learning with a set of labeled examples that correspond to the audio signatures, or patterns, of sounds associated with predetermined health events. Once the machine learning model is trained, audio event classifier 116 is capable of identifying types of health events from the input of feature vectors whose elements are features of sharp sound events captured in real-time and relayed to audio event classifier 116 from audio event detector 114. The features comprise features generated by feature generator 110 from audio signals corresponding to the sharp sound events. Optionally, the features generated through real-time processing of audio signals can be used to generate data structures for input to audio event classifier 116. The data structures can comprise feature vectors, matrices, or higher-order tensors whose elements are the features generated through real-time processing of audio signals.

Note that the multiple layers of the multilayered audio event classifier's audio pipeline are invoked only if a motion signature corresponding to a predetermined health event is identified by motion event determiner 102. Processing audio signals may consume a considerable amount of power. This is especially so with respect to processing audio signals, as in the present context, in which the goal of the signal processing is to distinguish between different types of sounds whose signal characteristics may be very similar—such as signals generated in response to an individual's cough and ones generated in response to the individual's throat clearing. Accuracy is gained from using a classifier such as a deep learning neural network, random forest, SVM, or other classifier but may come at a high cost in terms of power consumption. Using conventional techniques renders it difficult to perform an accurate classification using a platform such as earbuds or other wearable device having limited memory, battery power, and processing capabilities.

System 100 overcomes these constraints by initiating audio processing only in response to first identifying a potential event based on motion signals detected using a low-power detector, namely motion event determiner 102 which consumes relatively less power. The audio processing by multilayered audio event determiner 104 occurs sequentially using multiple layers with different levels of sensitivity and specificity. Each successive layer is invoked only if a preceding layer identifies signal attributes indicating a likely health event. Otherwise, audio processing ceases. Thus, the sequential processing further reduces processing and power consumption while not compromising the overall accuracy of detection of actual health events in contrast to conventional techniques.

In certain arrangements, motion event determiner 102 implements multi-centroid classifier 106. Multi-centroid classifier 106 is a novel, self-tuning classification model. Multi-centroid classifier 106 segregates segments of motion signals into distinct clusters. A specific cluster (or template) can identify a potential occurrence of a health event based on a unique "signature" (or pattern) of the segment of motion signals corresponding to the event. For example, an individual's coughing involves a series of motions of the head and neck as the individual inhales air into the lungs and expels the air in a burst-like fashion, which is trailed by a vocal phase. The head and neck motions can be detected, for example, with a motion sensor such as an IMU of an earbud worn by the individual. Multi-centroid classifier 106 identifies the cough based on the signature of the detected motion signals.

Motion signals whose signatures correspond to potential occurrences of health events (e.g., cough, wheeze, gasp) are positive samples and are assigned to one or more clusters thus separating the positive samples from negative ones—that is, motion signals not having signatures corresponding to a potential occurrence of a health event. Each cluster of the multi-centroid classifier provides a centroid as a template along with a threshold that defines the boundary of the cluster. The greater the number of clusters the more discriminating multi-centroid classifier 106 is. Each additional cluster, however, increases the run time for identifying whether an individual's motion indicates a potential occurrence of a health event. In order to automatically achieve a desired level of accuracy without unnecessarily increasing the run time, self-tuning multi-centroid classifier 106 iteratively splits clusters—beginning with an initial single clustering of an entire training set of examples—and continuing separating the different examples into distinct clusters until the desired level of accuracy is obtained.

Multi-centroid classifier 106 evaluates the performance of clusters at each iteration using a novel measure termed a discrepancy cost. The set of training examples is $\{X, Y\}$ where the X are samples represented by feature vectors whose elements are signal features and the Y are labels indicating each sample's classification. Positive samples (motion signals whose signature corresponds to potential occurrences of health events) can be identified as $X_p$ and negative samples as X. In the context of training multi-centroid classifier 106, M can indicate the number of positive samples, N the number of negative samples, and T the number of training iterations. At the t-th iteration, the number of clusters is $K_t$. $C_k$ is the centroid of the k-th cluster. Within the boundary defined by a threshold of the k-th cluster, $C_k$, k=1, . . . , $K_t$, there may be $M_k$ positive samples, $m_{ik}$, i={1, . . . , $M_k$}, and $N_k$ negative samples $n_{jk}$, j={1, . . . , $N_k$}. Multi-centroid classifier 106 at each iteration during training requires that every positive sample be assigned to at least one cluster. That is, for every t={1, . . . , T}, $$\cup_{k=1}^{K_t} \{m_{ik}:1, \ldots, M_k\} = X_p.$$

Ideally, the number of negative samples assigned to each cluster is zero, that is, $N_k=0$ for the k-th cluster. Accordingly, multi-centroid classifier 106 in reaching a desirable trade-off between accuracy and run-time overhead, minimizes the number of negative samples and maximizes the number of positive samples in the k-th cluster. For any cluster in which there is at least one negative sample among the positive samples, the positive samples should be closer to the centroid of the cluster than are any negative sample(s). For the k-th cluster, $C_k$, k=1, . . . , K (ignoring now the t subscript for simplification without loss of generality), multi-centroid classifier 106 determines the distance between each sample and the centroid $C_k$, obtaining $M_k+N_k$ distances. Multi-centroid classifier 106 thus configures the clustering with the aim of having the $M_k$ distances, $d(m_{ik}, C_k)$, $i=\{1, \ldots, M_k\}$ be smaller than the $N_k$ distances, $d(n_{jk}, C_k)$, $j=\{1, \ldots, N_k\}$. Thus, the objective of multi-centroid classifier 106 is to configure the clustering such that the $M_k \times N_k$ differences, $d(m_{ik}, C_k)-d(n_{jk}, C_k)$, are less than or equal to zero. Operatively, at each iteration, multi-centroid classifier 106 calculates with respect to each cluster the sum of all positive differences, $d(m_{ik}, C_k)-d(n_{jk}, C_k)$, and ignores the negative ones to compute a discrepancy cost given by the function $$L = \Sigma_{k=1}^{K} \Sigma_{i=1}^{M_k} \Sigma_{j=1}^{N_k} h(d(m_{ik}, C_k) - d(n_{jk}, C_k))$$

for all differences greater than zero. That is, $h(x)=x$ if $x>0$, and if $x<0$, $h(x)=0$.

The multi-centroid cluster is a discrepancy-based clustering that satisfies two requirements. Firstly, the assignment of a sample need not be determined by a single measurement but can instead use cluster averaging. Secondly, given the number of distinct clusters, the overall discrepancy cost defined by L is minimized.

Following is an example implementation in pseudo code of the training of the multi-centroid classifier based on the discrepancy cost:

```
input: Positive and negative training samples;
   stop criterion H
output: K templates C_k, k = 1, 2, ... K; and
   K thresholds
Initialize number of clusters K = 1;
Assign all the positive samples to cluster R_1;
Randomly select seed centroid C_1 from positive samples of cluster R_1;
Do discrepancy-based clustering with C_1 to obtain total cost L, update centroid
   C_1 and threshold;
While total cost L > stop criterion H Do
   Select R_t with the highest cost t = arg maxi L_i ;
   Randomly select two seed centroids from the positive samples of R_t;
   Do discrepancy-based clustering using K + 1 centroids C_1, ..., C_{K+1} to
      obtain total cost L, updated K + 1 centroids, and K + 1 thresholds;
   Calculate cost L_k for each of the K + 1 clusters;
   L = Σ_{k=1}^{K+1} L_k;
   K = K + 1;
end
```

Multi-centroid classifier 106 implements template matching by assigning a sample—that is, a motion segment that may or not correspond to a health event—to one of the trained model clusters (templates). Assignment is determined based on distances between the sample and each cluster's centroid. If a distance is smaller than a cluster's threshold (distance from the centroid to the boundary of the cluster), the inference is the sample is a positive sample. A positive sample corresponds to an event of interest—that is, a motion indicating a potential occurrence of a predetermined health event. In response to classifying a sample as positive, motion event determiner 102 initiates processing by multilayered audio event classifier 104 of the audio segment corresponding to the motion segment (positive sample). Otherwise, multilayered audio event classifier 104 remains dormant and no energy is expended in the processing of the audio segment.

Figure 5:
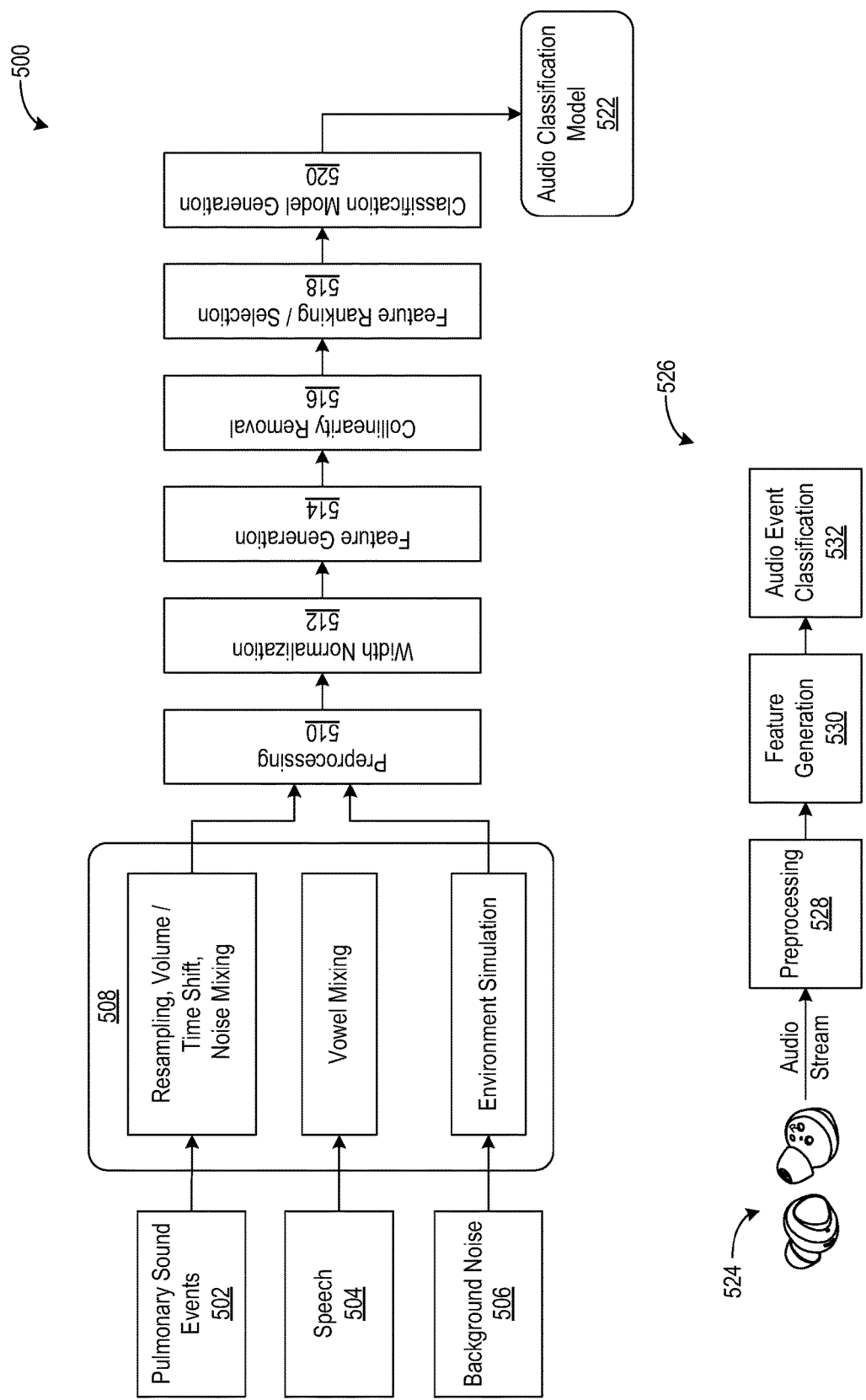
FIG. 5 illustrates an example application of the system of FIG. 1 in detecting and identifying health events corresponding to pulmonary episodes.

FIG. 5 illustrates an example application 500 of system 100. Application 500 pertains to detecting and identifying health events that correspond to pulmonary conditions and episodes. The health events associated with pulmonary conditions and episodes include physiological events such as coughing, wheezing, gasping, and the like. Such physiological events are health events that can indicate a pulmonary condition such as COPD, bronchitis, or lung infection (e.g., Covid-19), or a pulmonary episode such as an asthmatic attack.

Detecting and identifying health events corresponding to pulmonary conditions and episodes requires a classification model that can classify audio signals indicating a cough, wheeze, gasp, or similar health event. The classification model can be trained using labeled examples of audio signals that illustratively include pulmonary sound events 502, speech 504, and background noise 506. One group of labeled examples can include sharp pulmonary sounds of interest (e.g., cough). Another can comprise continuous non-sharp sounds. Still another can comprise background noise and periods of silence. During training of the classification model, an optional augmentation layer 508 can illustratively perform various audio signal manipulation procedures. The procedures can include resampling, volume and time shifting, and/or noise mixing of pulmonary sound events 502. The procedures also can include vowel mixing speech 504 and environmental simulation of background noise 506. The various augmentation procedures can improve the sensitivity of the classification model.

The audio signals can undergo preprocessing 510 and width normalization 512 of segments of the audio signals. Feature generation 514 extracts relevant acoustic features, which can include temporal features such as mean, standard deviation, zero crossing rate, and rms energy, as well as spectral features such as spectral density, MFCC, and chroma. Collinearity removal 516 optionally reduces processing by eliminating highly correlated features. Other features can be selected based on feature ranking 518. The selected features can be arranged as elements of feature vectors, matrices, or higher-order tensors (labeled examples) and used for classification model generation 520. Classification model generation 520 can comprise supervised learning to generate a machine learning model such as a deep learning neural network, random forest, or other machine learning model.

The training phase of application 500 concludes by outputting audio classification model 522. The same procedures, though described in the context of training a model to detect and identify health events corresponding to pulmonary episodes and conditions, can be used in training a classification model to detect and identify other health events. Other health events can include, for example, health events corresponding to nutritional monitoring, mental health assessments, and diagnosis of sleep disorders. Different types of classification models are trained using various other types labeled training examples (audio samples) to train audio classification model 522 for detecting and identifying other types of health events.

Once audio classification model 522 is trained, it can be used by system 100 implemented in a device such as a portable device or wearable. Illustratively, with respect to application 500, system 100 is implemented in earbuds 524. With system 100 implemented in earbuds 524, real-time motion signals can be generated by an earbud IMU that responds to head and neck movements of the user caused by the user's coughing, wheezing, and the like. The user movements can be identified through template matching using templates that specifically correspond to a potential occurrence of a predetermined health event such as a cough, wheeze, or gasp associated with a pulmonary episode or condition. In response to detecting to a potential occurrence of a predetermined health event, audio processing 526 by system 100 is invoked. System 100 illustratively performs preprocessing 528 of audio signals linked to the motion signals corresponding to the potential occurrence of a predetermined health event. Linking audio signals with motion signals, as described above, can be performed using a sliding window. System 100 illustratively performs feature generation 530, generating relevant acoustic features such as temporal features (e.g., mean, standard deviation, zero crossing rate, rms energy) and spectral features (e.g., spectral density, MFCC, chroma). System 100 performs audio event classification 532 by separating out and discarding non-voice activity (e.g., background noise). Features corresponding to voice activity are processed for sharp sounds indicating a possible a health event corresponding to a pulmonary condition or episode.

In the present context of application 500, sharp sounds are ones having high volume levels that are, or that resemble, abrupt pulmonary sounds such as coughing, gasping, sneezing, wheezing, throat clearing, and the like. Non-sharp sounds are discarded. Sharp sound features can be arrayed in feature vectors, matrices, or higher-order tensors (e.g., as elements of one or more feature vectors). The features of the sharp sounds are input to the now-trained audio classification model 522. Based on the model classification, system 100 identifies whether the potential occurrence is in fact an actual occurrence of a predetermined health event. If so, system 100 identifies the type as a cough, gasp, wheeze, or other health event associated with a pulmonary condition or episode. It is noted again that the classification can be a complex process. Nevertheless, audio event classification 532 is performed only if sharp sounds are detected and only with respect to the features specifically associated with the sharp sounds. All other audio data is discarded. By invoking audio event classification 532 only with respect to sharp sounds, system 100 is more readily and efficiently implemented in a low-resource platform such as a wearable device (illustratively, earbuds 524).

Figure 6:
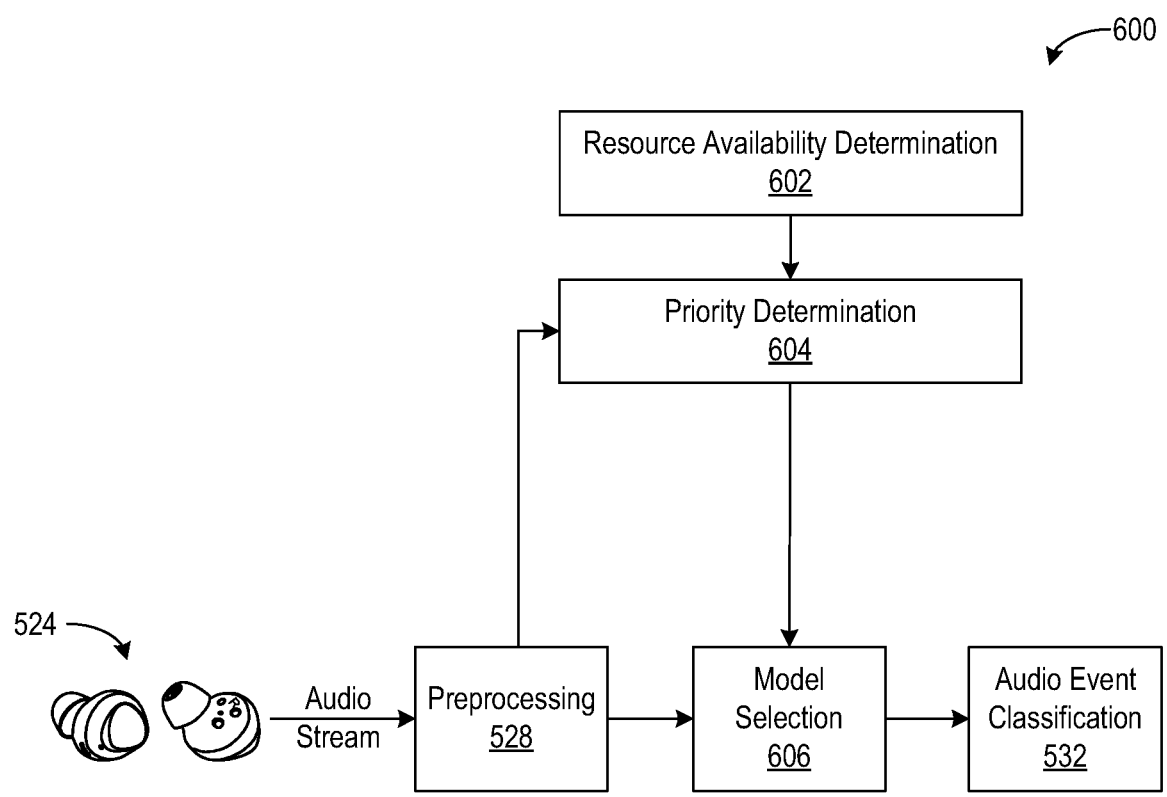
FIG. 6 illustrates an example context-aware model selection optionally performed by the system of FIG. 1.

FIG. 6 illustrates an example context-aware model selection 600 optionally performed by system 100. Context-aware model selection 600 further enhances system 100's achieving of an efficient trade-off between classification accuracy and conservation of resources used by system 100, enabling system 100 to be implemented effectively in a resource-limited platform (e.g., earbuds). When system 100 is implemented in a resource-limited platform such as a portable device or wearable, system 100 can operate in conformance with predetermined processing and memory constraints. The predetermined constraints can be dictated by a ranking of the importance of the various tasks performed by the resource-limited platform. For example, if system 100 is implemented in earbuds 524, processing and memory resources, as well as battery usage, can be prioritized to enable earbuds 524 to be used for listening to music and/or handling phone calls.

Resource availability determination 602 can be performed by system 100 at any point during monitoring a user's movement. In certain arrangements illustrated in FIG. 6, preprocessing 528 is invoked in response to detecting user movements indicating a potential occurrence of a predetermined health event. In response to an invocation of audio processing, system 100 elicits resource information from earbuds 524 and makes resource availability determination 602. Resource availability determination 602 can reveal, for example, the current processing and/or memory capabilities of earbuds 524 given other on-going processes performed by earbuds 524, such as handling calls and/or playing music. Resource availability can also include remaining battery life of earbuds 524. Based on resource availability determination 602, system 100 makes priority determination 604. Based on priority determination 604, system 100 makes model selection 606, choosing the classification model used for audio event classification 532. System 100 can choose the model based at least in part upon the model's complexity—which, accordingly, dictates the amount of power consumed by audio event classification 532. Thus, the type of classification model (e.g., deep learning neural network, random forest, SVM) can be selected to dynamically adjust total power consumption of system 100 as implemented in the resource-limited platform (illustratively, earbuds 524).

Alternatively, audio event classification 532 can be disabled altogether based on resource availability determination 602 (e.g., low battery). Suspending audio event classification 532 can preserve power as necessary. In certain arrangements, operation of audio event classification 532 can be suspended unless and until system 100 detects a user movement indicating a potential occurrence of a predetermined health event. In such arrangements, a confirmation of the serious health event is obtained by temporarily resuming audio event classification 532 that detects whether the predetermined health event likely occurred and, if so, identifies the type of health event.

Figure 7:
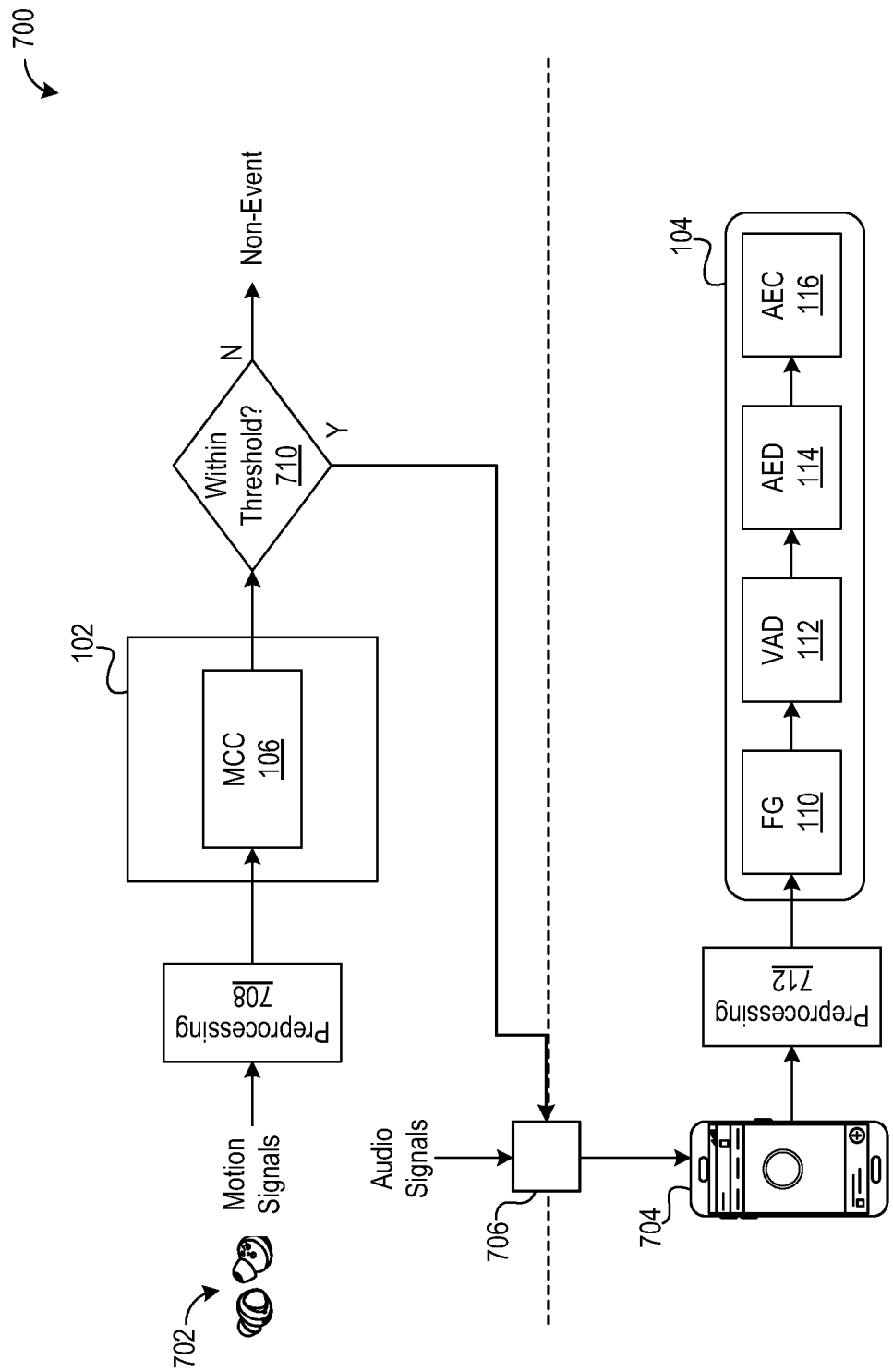
FIG. 7 illustrates an example multi-device allocation of elements of the system of FIG. 1 in accordance with certain arrangements.

FIG. 7 illustrates an example multi-device allocation 700 of system 100 elements in accordance with certain arrangements. Multi-device allocation 700 implements separate elements of system 100 in different devices. Illustratively, motion event determiner 102 is implemented in earbuds 702, while multilayered audio event classifier 104 is implemented in an auxiliary device 704, such as a smartphone or cloud-based server. Earbuds 702 can communicatively couple with auxiliary device 704 via gateway 706. Although performing the processing functions in a single device limits the amount of data that needs to be communicated to an auxiliary device, there are circumstances where it can be advantageous to offload some of the processing to one or more auxiliary processors. This is especially so where multiple processing demands are placed on the processor of a limited-resource platform such as earbuds 702, which performs multiple other functions, such as handling phone calls and/or playing music. Allocation of operations 700 reduces the processor load and power consumption of such limited-resource platforms.

Operatively, an IMU embedded in earbuds 702 generates motion signals. Earbuds 702 perform preprocessing 708 and convey the signals to motion event determiner 102, which is implemented in earbuds 702. In certain arrangements, motion event determiner 102 performs the template matching using multi-centroid classifier 106. If determination 710 of multi-centroid classifier 106 is that a motion event generated based on the motion signals is within the boundary threshold of a cluster, then motion event determiner 102 invokes audio processing. Audio processing can be invoked by a signal from earbuds 702 via gateway 706 to auxiliary device 704. Auxiliary device 704 can acquire audio signals linked to the motion signals and corresponding to a potential occurrence of a predetermined health event from earbuds 702. Alternatively, or additionally, if auxiliary device 704 is a device such as a smartphone or other device located sufficiently close to the user, auxiliary device 704 can itself acquire audio signals linked to the motion signals and corresponding to a potential occurrence of a predetermined health event.

Auxiliary device 704 performs preprocessing 712 and conveys the audio signals to multilayered audio event determiner 104. The elements of multilayered audio event determiner 104—feature generator 110, voice activity detector 112, audio event determiner 114, and audio event classifier 116, as described above—process the audio signals. Audio event classifier 116 determines whether a health event has in fact occurred and, if so, identifies the type based on classification of the health event using a machine learning classifier model. Otherwise, if at any layer of multilayered audio event determiner 104 it is determined that the audio signals cannot correspond to a health event, multilayered audio event determiner 104 discards the audio signals without further processing.

In certain arrangements, all or a select subset of the functions of system 100 can be implemented in one of a pair of earbuds, with the other earbud serving as the auxiliary device. Thus, for example, if the battery life of one earbud is less than a predetermined threshold, then the functions can be re-allocated to the other earbud. As described below, the re-allocation from the one earbud to the other can also be performed in response to a misalignment of the one earbud in the user's ear whenever the misalignment likely impedes the performance of system 100.

Figure 8:
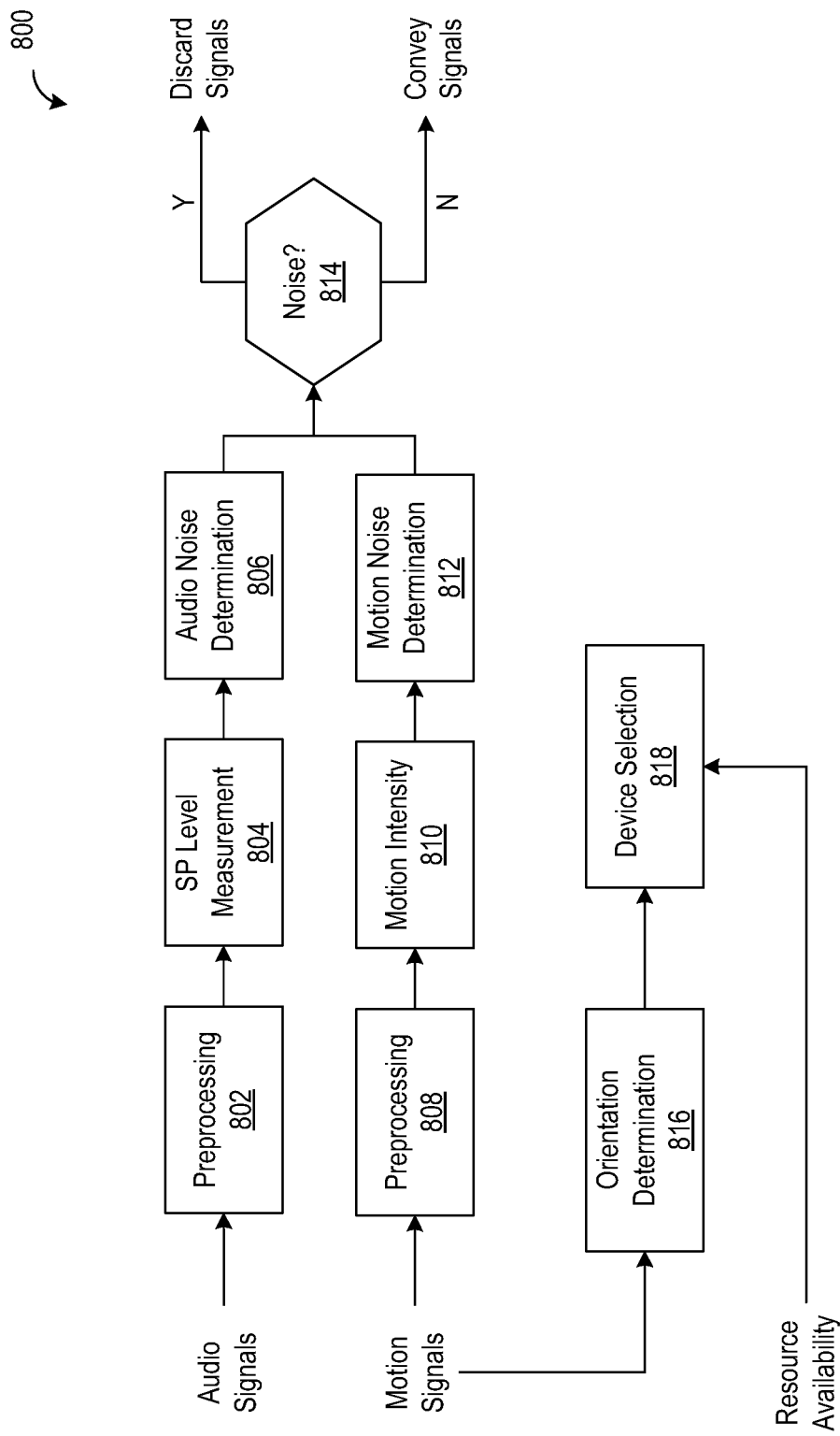
FIG. 8 illustrates an example data quality determination optionally performed by the system of FIG. 1.

FIG. 8 illustrates an example data quality determination 800 optionally performed by system 100. In one aspect, data quality determination 800 mitigates the degrading effect of noise in the audio and/or motion signals that are processed by system 100. In another aspect, data quality determination 800 can prompt a reallocation of operations of system 100 among multiple devices. Data quality determiner 800 prompts a reallocation in response to determining that a depletion of resources (e.g., battery power) of one of the devices is likely to degrade the quality of the device's performance in implementing one or more operations of system 100. In still another aspect, data quality determination 800 prompts a reallocation in response to determining that an improper alignment of a wearable device (e.g., earbud) is likely to degrade the quality of the wearable device's performance in implementing system 100.

Data quality determination 800 is based on measuring the acoustic and motion signals for noise to identify suspect segments that potentially affect the quality of the signals. Data quality determination 800 includes signal preprocessing 802 of audio signals. Signal preprocessing 802 generates a time-based measurement of the sound pressure level 804 based on which audio noise determination 806 is made. In certain arrangements, audio noise determination 806 is an $L_n$ measurement over a specific time interval. $L_n$ measures the n-percent of time over the time interval that the audio level exceeded a predetermined level, L. $L_n$ can indicate a sound level of noise that likely masks ordinary sounds associated with predetermined health events (e.g., cough, gasp, wheeze). $L_n$ can be obtained by a statistical analysis of various types of noise. With respect to the corresponding time interval, data quality determination 800 includes signal preprocessing 808 of motion signals. Signal preprocessing 808 generates motion intensity 810, a time-based measurement based on which motion noise determination 812 is made. If determination 814 is that either the audio signals or motion signals are degraded by noise, then the signals are discarded. Otherwise, the motion and audio signals are conveyed to the other elements of system 100 for additional signal processing as already described.

With system 100 implemented in a wearable device, data quality determination 800 also can determine the orientation of the wearable device. If orientation of the wearable device is such that the motion signals obtained with the device are degraded, then system 100 can allocate certain operations from one device to an alternative device. Data quality determination 800 makes orientation determination 816 based on motion signals generated by a device motion sensor (e.g., earbud IMU). System 100 makes device selection 818 in response to the determination. For example, if system 100 is implemented in one of a pair of earbuds that is ill positioned for detecting motions of the user, then in response to data quality determination 800, system 100 can prompt the other earbud to capture the motion signals for processing. Similarly, if based on data quality determination 800 certain resources of a device are discovered to be to too limited to generate or process audio or motion signals with sufficient quality, then system 100 based on resource availability information can allocate system 100 operations to one or more alternate devices. For example, as described above, if system 100 is implemented in one of a pair of earbuds whose battery level is low, then based on data quality determination 800, system 100 can prompt the other earbud to capture the motion signals for processing.

Figure 9A:
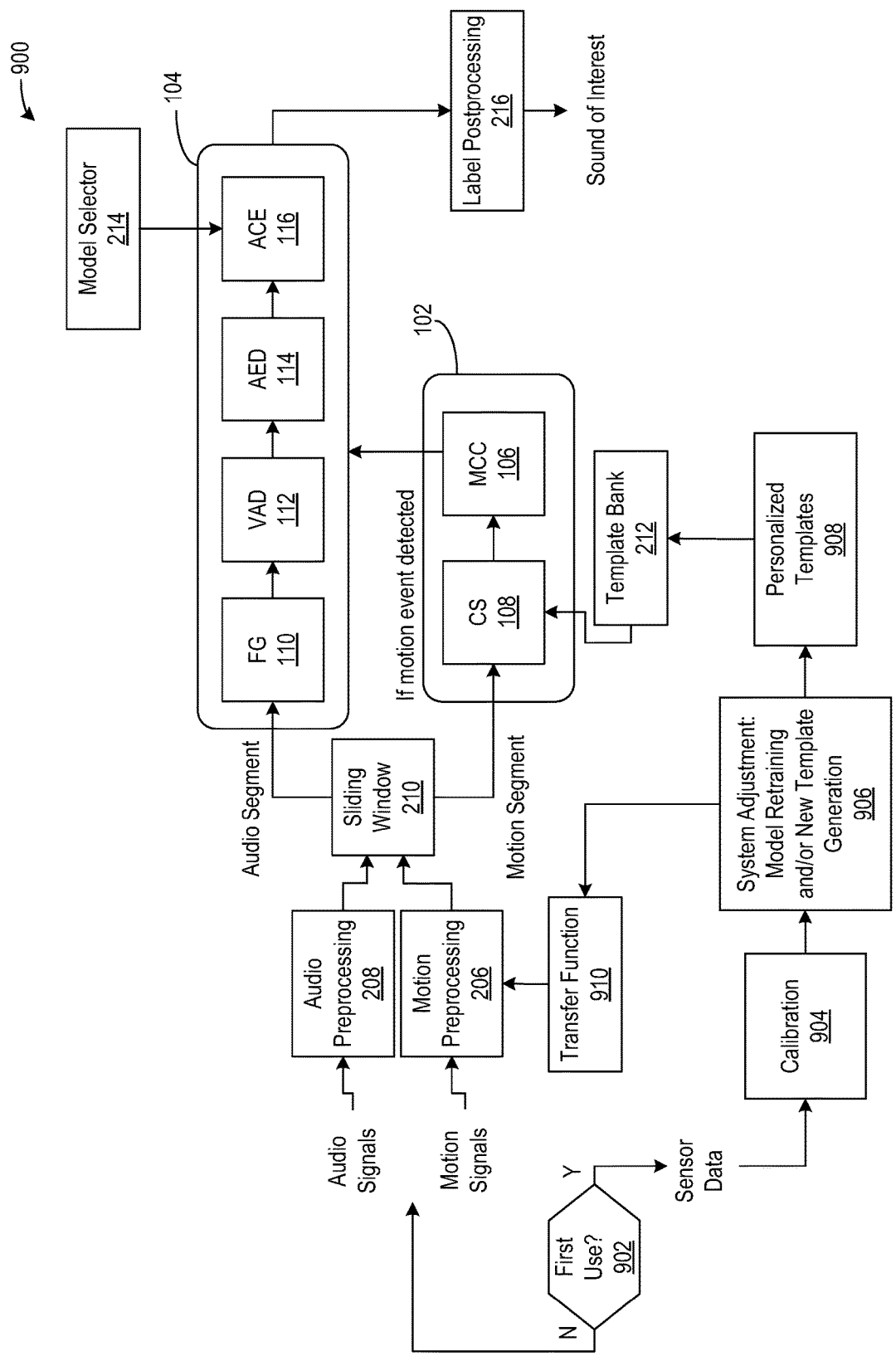
FIGS. 9A, 9B, and 9C illustrate an example calibration optionally performed by the system of FIG. 1.
Figure 9B:
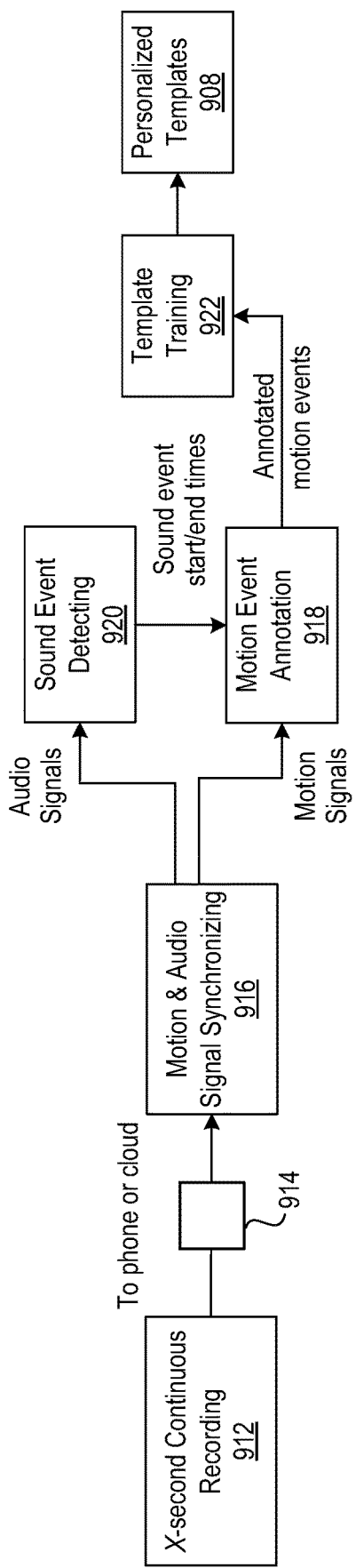
Figure 9C:
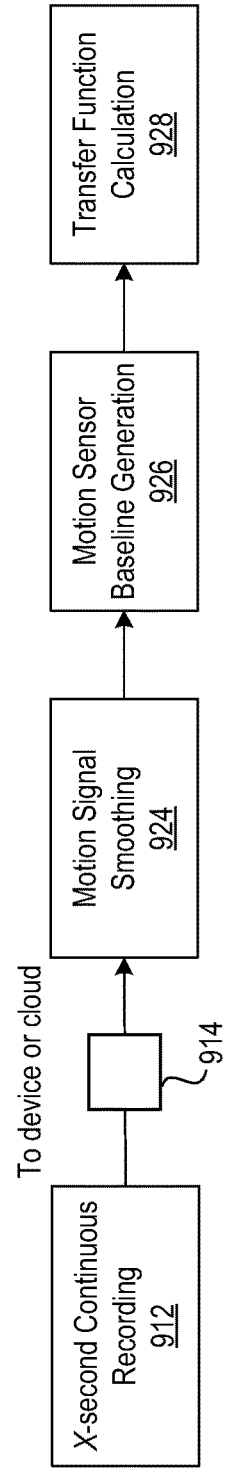

FIGS. 9A-9C illustrate an example orientation calibration 900, which is optionally performed by system 100. Orientation calibration 900 can mitigate the effects of manufacturing variation on the device in which system 100 is implemented. Relatedly, orientation calibration 900 can mitigate the effect of an ill fit of a wearable device, given a specific user's body type. Due to variation in device manufacturing and/or differences in body type, a wearable device may fit different users differently. For example, the orientation of an earbud may depend on the shape of a user's outer ear, and as a result, the orientation of an IMU unit embedded in the earbud may vary from one user to another. Such variation affecting device orientation when worn by a user can adversely affect the ability of the device to generate reliable motion signals in response to a user's movement. System 100, as described above, uses template matching in which the amplitude and direction of the motion signals are matched with pre-trained default templates. If orientation of the motion sensor (e.g., earbud IMU) of the user's wearable deviates by more than a predetermined threshold from orientation used in training the templates for matching, system 100's accuracy detecting and identifying a health event may be adversely affected. Orientation calibration 900 mitigates the likelihood of such an adverse effect by calibrating system 100 for use by specific users.

As illustrated in FIG. 9A, orientation calibration 900 is optionally invoked by determination 902. If the wearable device (e.g., earbuds) implementing system 100 is being worn by a user for the first time, calibration 904 is initiated. Calibration 904 can last a brief time (e.g., 30 seconds). During calibration 904 the motion sensor of the wearable is calibrated while the device is being worn by the user, and the motion sensor is generating motion signals in response to the user's movement. Based on calibration 904, system adjustment 906 is performed. System adjustment 906 can include generating user-specific personalized templates 908 for retraining the template matching model implemented by system 100 in detecting potential occurrences of one or more predetermined health events. Personalized templates 908 can be added to template bank 212 of system 100. Additionally, or alternatively, system adjustment 906 can include acquiring a user-specific baseline for motion sensor (e.g., IMU) components and generating transfer function 910 to correct for baseline changes when making inferences using the template matching model.

FIG. 9B illustrates an example calibration for acquiring user-specific templates for retraining the template matching model. Optionally, calibration 904 includes recording of audio and motion signals generated, respectively, by a sound transducer (e.g., microphone) and motion sensor (e.g., IMU) of the device in which system 100 is implemented. For example, the user may be asked to perform certain actions as the recording of audio and motion signals is generated. For example, the user may be asked to cough a specified number of times, possibly with intermittent pauses of a designated duration, while remaining stationary. The motion and audio signals generated in response thereto may be recorded for a certain time (e.g., x-seconds) generated x-second continuous recording 912. If the device in which system 100 is implemented is a wearable (e.g., earbuds), then it can be advantageous to perform at least certain portions of orientation calibration 900 in conjunction with an auxiliary device (e.g., cloud-based server, smartphone) communicatively coupled with the wearable. Optionally, therefore, x-second continuous recording 912 can be conveyed to the auxiliary device via gateway 914. Orientation calibration 900 can include motion and audio synchronizing 916. Sound event detecting 920 timestamps start and end times of specific sound events. Motion event annotation 918, based on the timestamping, annotates the motion signals to generate annotated motion events (labeled examples). The annotated motion events provide the training examples used for template training 922, which generates personalized templates 908.

FIG. 9C illustrates an example calibration for acquiring a user-specific baseline for motion sensor (e.g., IMU) components and generating transfer function 910 to correct for baseline changes when making inferences using the template matching model. Illustratively, x-second continuous recording 912 generated as described above can be conveyed to the auxiliary device via gateway 914. Motion signal smoothing 924 smooths the recorded motion signals. Motion sensor baseline generation 926 provides a baseline against which user-specific motions are measured. The baseline is used for transfer function calculation 928, which yields transfer function 910. Transfer function 910 can provide an offset or correction to baseline changes when event determiner 102 makes a real-time determination using the template matching model whether a motion event is a potential occurrence of a health event.

Figure 10:
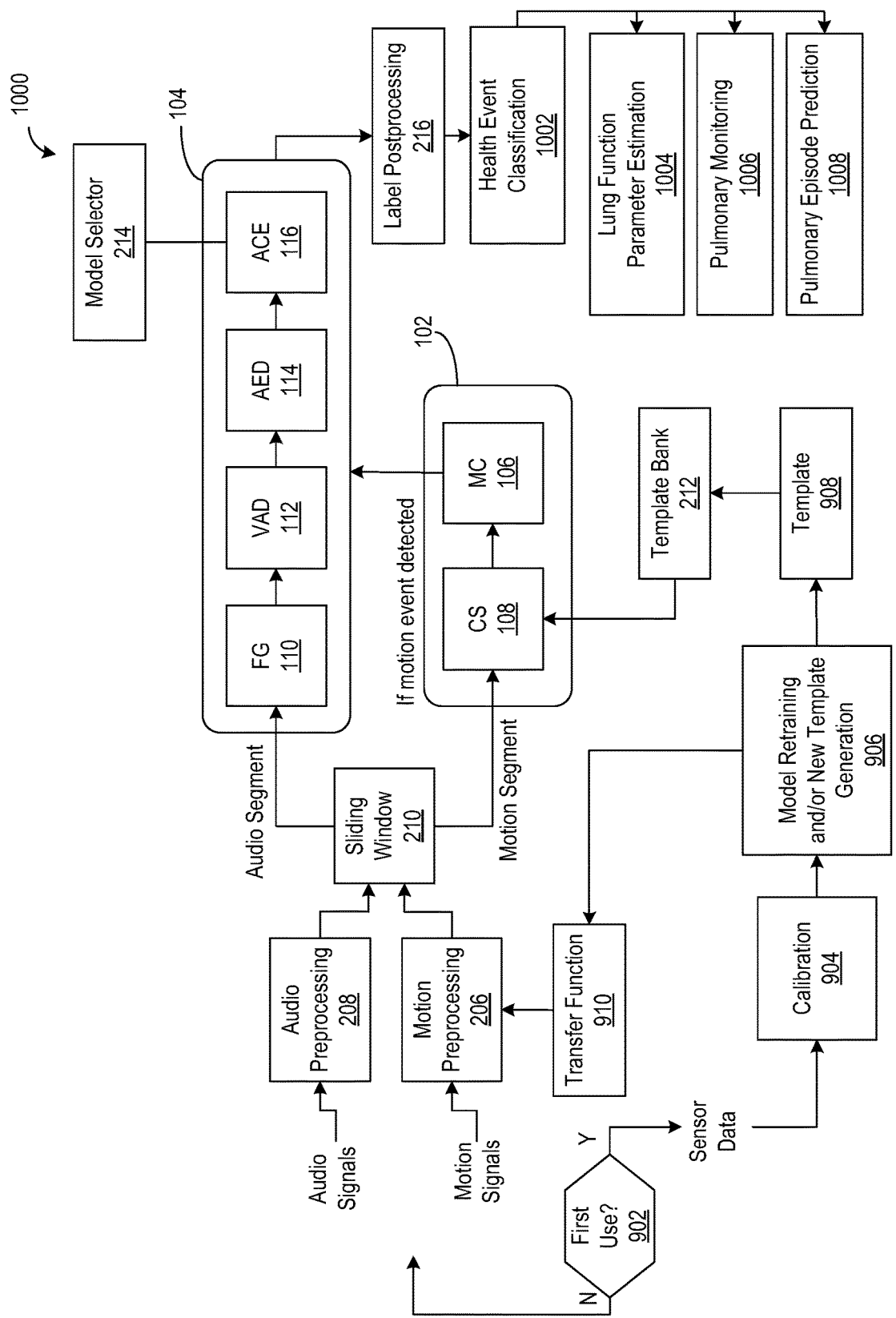
FIG. 10 illustrates an example lung function estimation and pulmonary condition monitoring by the system of FIG. 1.

FIG. 10 illustrates an example lung function estimation and pulmonary condition monitoring 1000 by system 100. The above-described audio processing of audio signals by multilayered audio event classifier 104 is invoked by motion event determiner 102 in response to determining that detected motion signals are likely an occurrence of a predetermined health event. The health event can be a cough, wheeze, or other health event corresponding to a pulmonary condition or episode. If features of audio signals linked to the motion signals reach the last layer of multilayered audio event classifier 104, a machine learning model identifies the likely health event. Label postprocessing 216 affixes an electronic label that identifies the audio signals as corresponding to identified health event (e.g., cough, wheeze, gasp). Once accurately identified and labeled by system 100, the audio signals can undergo further signal processing to estimate the user's lung function. For example, the lung mechanism of a cough involves inhalation, air compression, and forced exhalation—mechanisms measured using spirometry testing. It has been shown that an obstruction of lung airways can have a similar effect on cough features and spirometry measures, and accordingly, pulmonary conditions such as lung obstruction can be estimated using acoustic features of an individual's cough. Similar, wheezing has been shown to be a prominent system of various obstructive pulmonary diseases.

Illustratively, system 100 performs the above-described functions, and in doing so, generates health event classification 1002. Health event classification 1002 identifies audio signals captured with the device in which system 100 is implemented. The audio signals, labeled by label postprocessing 216, can be conveyed to one or more other devices. Using the captured and identified audio signals, the other device(s) can perform lung function parameter estimation 1004. Lung function estimation can include estimation of forced expiratory volume (FEV1), forced expiratory volume to vital capacity ratio (FEV1/FVC), and other/or other pulmonary parameters. The other device(s) can perform pulmonary monitoring 1006 by periodically estimating pulmonary parameters. The other device(s) can perform pulmonary episode prediction 1008 and can generate a warning in response to detecting, for example, coughing, wheezing, or other physiological event indicating a likely near-term occurrence of a pulmonary episode.

Advantageously, system 100 can be implemented in a portable device or wearable, such as earbuds. The multilayered sensor fusion architecture of system 100 enables system 100 to be implemented efficiently in such devices. System 100 manages usage of the device's resources so as not to unduly limit the device's ability to perform other functions (e.g., handling calls, playing music). System 100 does so while maintaining performing detection and identification of health events with accuracy. Efficient use of device power also enables longer-term monitoring by system 100 using a portable device or wearable.

Figure 11:
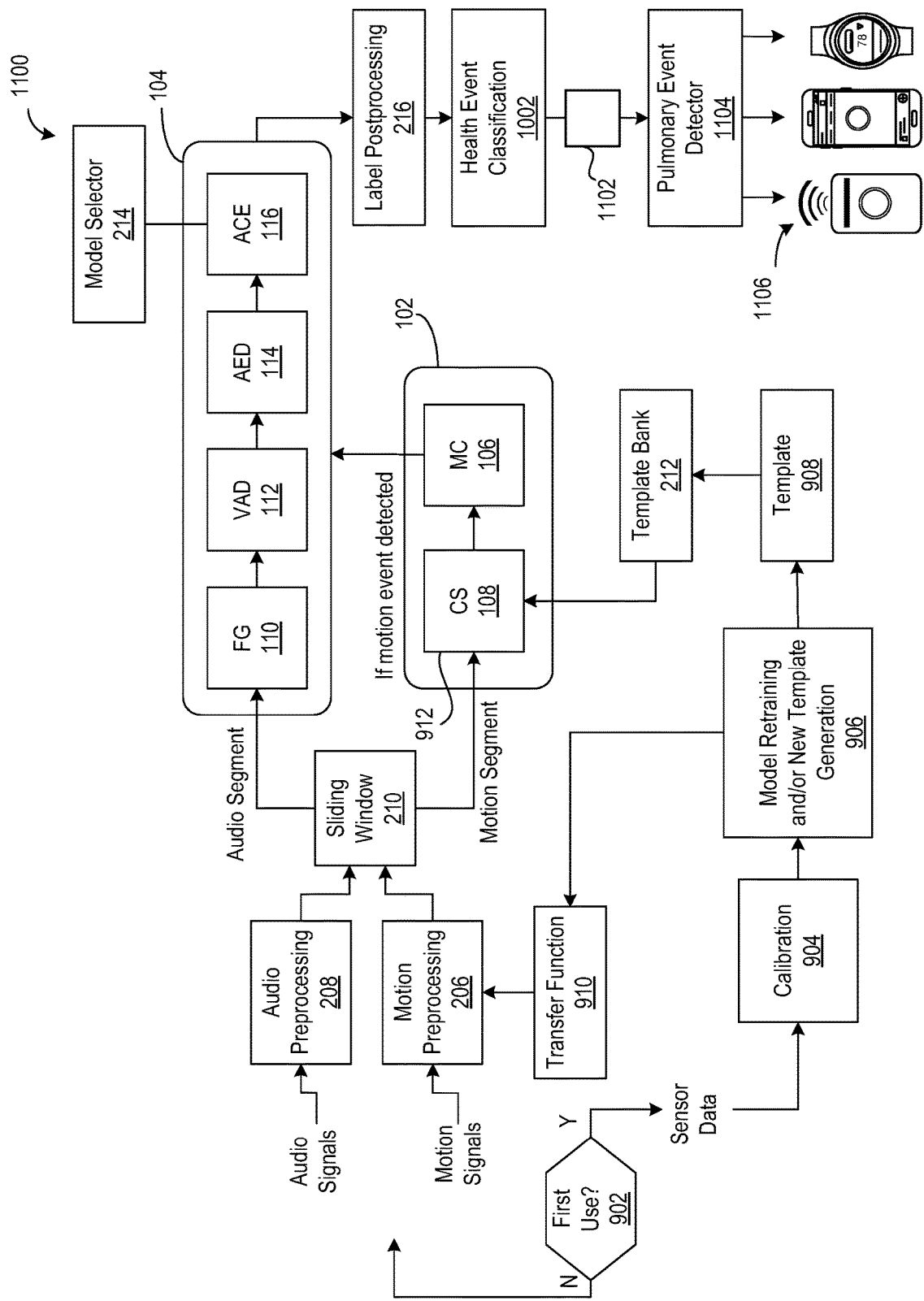
FIG. 11 illustrates an illustrates an example lung function estimation and pulmonary condition monitoring by the system of FIG. 1 using multiple devices.

FIG. 11 illustrates example lung function estimation and pulmonary condition monitoring 1100 by system 100 using multiple devices. As described, system 100 can detect and identify a health event based on device-captured motion and audio signals. Multilayered audio event classifier 104 identifies the health event and the corresponding audio signals labeled with health event classification 1002. Health event classification 1002 and the identified audio signals are illustratively conveyed to pulmonary event detector 1104. Optionally, given that system 100 may be implemented in a limited-resource platform such as earbuds or other wearable, health event classification 1002 and the identified audio signals can be conveyed to pulmonary event detector 1104 via gateway 1102 to a separate device that implements pulmonary event detector 1104. The device can be an auxiliary device having greater processing capability and/or memory.

Illustratively, pulmonary event detector 1104 is implemented in multiple devices 1106. Multiple devices 1106 can include, for example a smartphone, smartwatch, virtual assistant, and/or another such device. One or more of multiple devices 1106 can also capture pulmonary events of interest. A cooccurrence of evaluations made with multiple devices 1106 can provide enhanced confidence in the accuracy of the detection and identification of health events corresponding to a pulmonary condition or episode.

Figure 12:
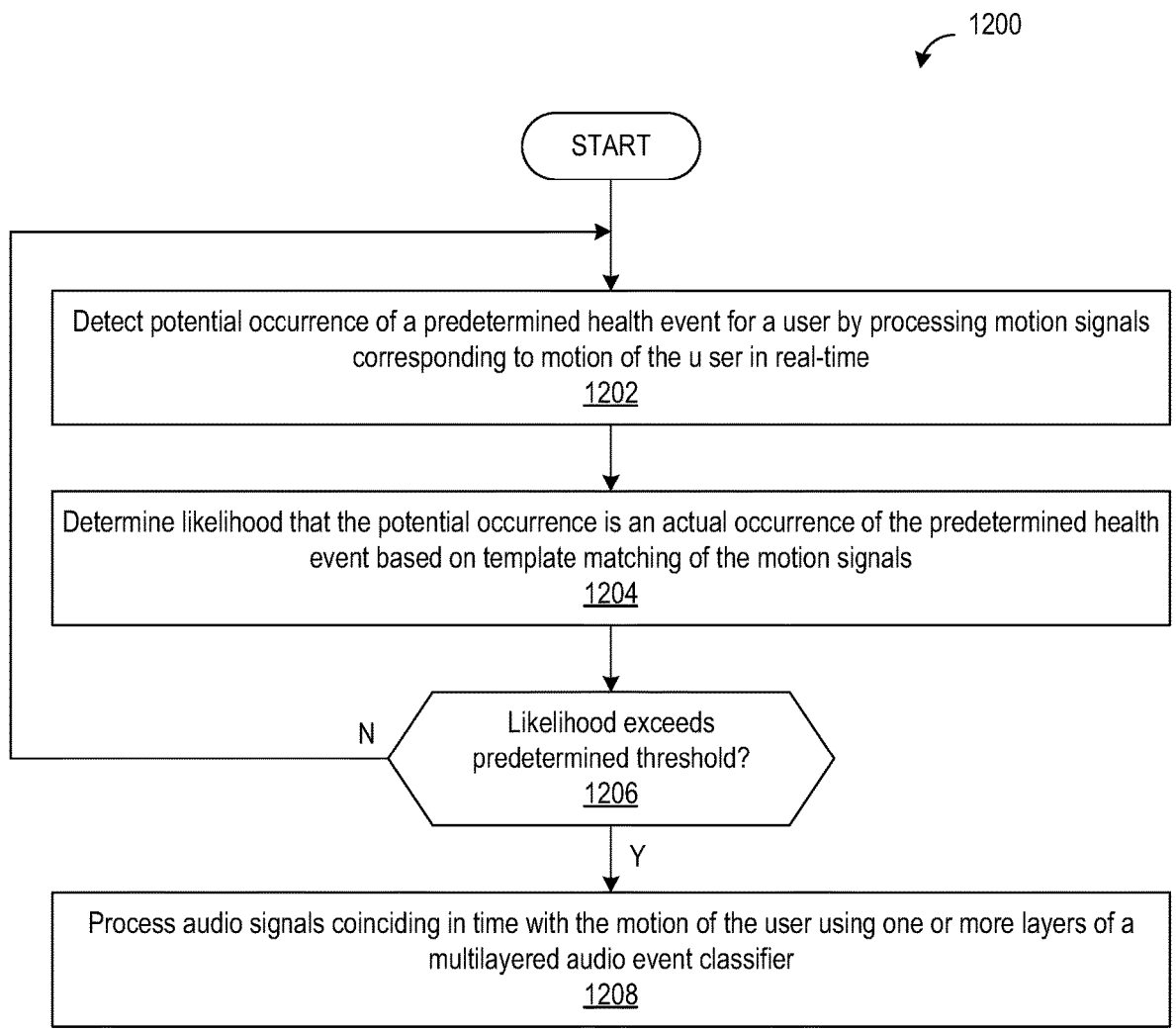
FIG. 12 illustrates an example method of determining a health event.

FIG. 12 illustrates an example method 1200 of determining health events in response to motion and audio signals. Method 1200 can be performed by a device (or device operatively coupled to one or more auxiliary devices) including a health event determining system as described herein (collectively "the system").

The system at block 1202 can detect a potential occurrence of a predetermined health event for a user. The system can detect the potential occurrence by processing in real-time motion signals generated by one or more motion sensors in response to motion of the user. The motion signals can be generated by the motion sensor(s) and correspond to motion of the user.

At block 1204, the system can determine a likelihood that the potential occurrence is an actual occurrence of the predetermined health event. The determination can be the system performing on template matching of the motion signals.

The system at decision block 1206 determines whether the likelihood exceeds a predetermined threshold. For example, the threshold may be a 90 percent, 95 percent, or other likelihood threshold. If the likelihood does not exceed the predetermined threshold the system takes no further action with respect to the motion signals. The system can continue monitoring sensor-generated motion signals to detect the possible occurrence of a predetermined health event of the user.

In response to determining at decision block 1206 that the likelihood exceeds the predetermined threshold, the system processes audio signals coinciding in time with the motion of the user. The system can process the audio signals using one or more layers of a multilayered audio event classifier.

In certain arrangements, the multilayered audio event classifier filters the audio signals in response to detecting voice activity. The filtering can separate the audio signals that correspond to voice activity from audio signals corresponding to non-voice activity. Otherwise, the system ceases processing and discards the audio signals. In response to detecting one or more sharp sound events within the audio signals corresponding to voice activity, the system can process the audio signals corresponding to voice activity to separate the one or more sharp sound events contained therein from non-sharp sound events. Otherwise, the system can cease processing and discard the audio signals. In response to detecting sharp sound events, the system at a final layer of multilayered audio event classifier can classify the sharp sound events using a machine learning classifier. Based on classifying the sharp sound events, the system can identify the health event.

In some arrangements, the system selects the machine learning classifier from a plurality of machine learning classifiers. The machine learning classifiers can differ in complexity. A model's complexity can determine the resources needed to classify features of audio signals. The resources include, for example, the extent and/or duration that the system's processors and/or memory are utilized in classifying audio signal features using a particular machine learning classifier. The model complexity thus also affects the amount of power consumed in performing the classification. Relatedly, therefore, the model complexity can affect or impede the system's ability to perform other functions (e.g., handling calls, playing music). In making a classification, the system can choose a classification model whose complexity is not likely to impede performance of one or more other functions. For example, if the system is performing a function such as handling a call or playing music, the system can select a less complex machine learning model to classify a sound event. For example, if the level of a battery powering the system is low, the system can select a less complex classification model for classifying the sound event. Thus, the system can select a machine learning classifier based on the machine learning classifier's complexity and the system resources required for implementing the machine learning classifier.

In other arrangements, the system conveys the audio signals to an auxiliary device communicatively coupled with the device. The auxiliary device can implement the multilayered audio event classifier and perform the processing of the audio signals with the multilayered audio event classifier. The system can convey the audio signals to the auxiliary device in response to detecting that a power level of the device is less than a predetermined threshold. In some arrangements, the device that performs motion signal processing is a wearable device (e.g., earbuds) and the auxiliary device comprises a plurality of auxiliary devices.

In using multiple devices, the system can detect that a wearable device is positioned to impede generating at least one of the motion signals or the audio signals using one or more sensors of the wearable device. For example, an earbud may be ill fitted within the outer of the user. The system can respond by automatically selecting one of the plurality of auxiliary devices for generating the motion signals and/or the audio signals.

In still other arrangements, the system can detect acoustic noise and/or motion noise above a predetermined threshold within a selected segment of at least one of the motion signals or the audio signals. In response to detecting noise above a threshold, the system can respond by discarding any noise-affected motion or audio signal.

In certain arrangements, the system can detect health events corresponding to a pulmonary condition or episode. The system can be used in performing lung function parameter estimation in response to detecting and identifying a health event corresponding to a pulmonary condition, episode, or other pulmonary event.

In certain other arrangements, the system can perform an orientation calibration. The orientation calibration can include generating a user-specific template for retraining a model used for the template matching. The orientation calibration can include generating a transfer function based on a user-specific baseline for calibrating a motion sensor for sensing the real-time motion signals.

Figure 13:
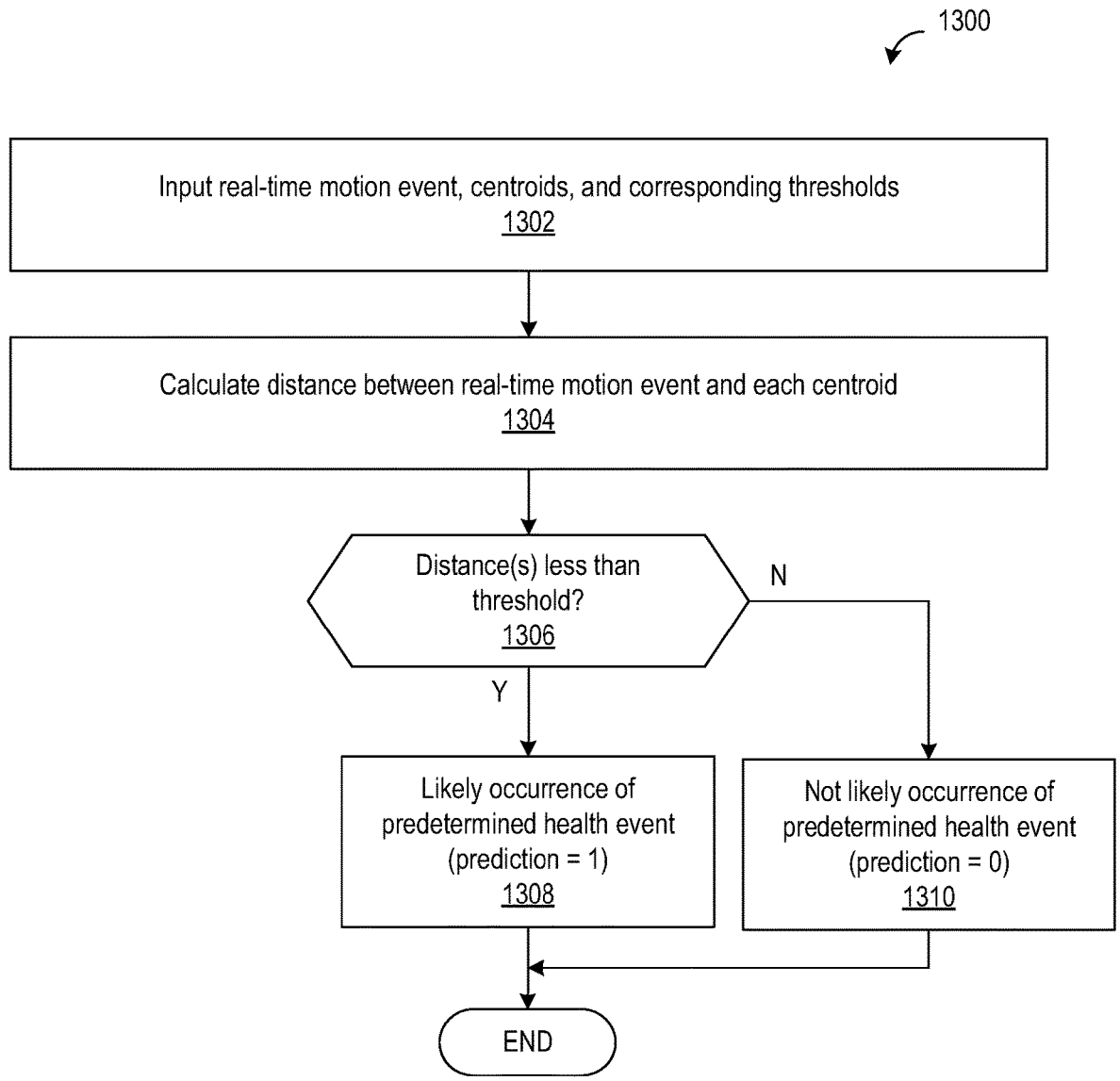
FIG. 13 illustrates a method of performing motion signal classifications using a multi-centroid classifier.

FIG. 13 illustrates an example method 1300 of classifying motion signals based on template matching using the multi-centroid classifier. Method 1300 can be performed by a device (or device operatively coupled to one or more auxiliary devices) including a health event determining system as described herein (collectively "the system").

At block 1302, the system inputs a real-time sample of a motion event, centroids, and corresponding thresholds. The motion event (a motion signal-based event sample) can be represented as a point in an n-dimensional space. Centroids are center points of clusters (templates), whose boundaries are the corresponding thresholds.

At block 1304, the system calculates the distance between the motion event, or sample, and each centroid. If at decision block 1306 any of the distances are less than a cluster's threshold, then the motion event is identified at block 1308 as a positive sample (prediction=1), meaning that the sound event likely corresponds to a predetermined health event represented by a cluster (or template). Otherwise, the sound event is identified at block 1310 as not likely an occurrence of a predetermined health event (prediction=0). If the prediction equals one, then the system invokes processing of audio signals corresponding to the motion event. If the prediction equals zero, the motion and audio signals are discarded.

Figure 14A:
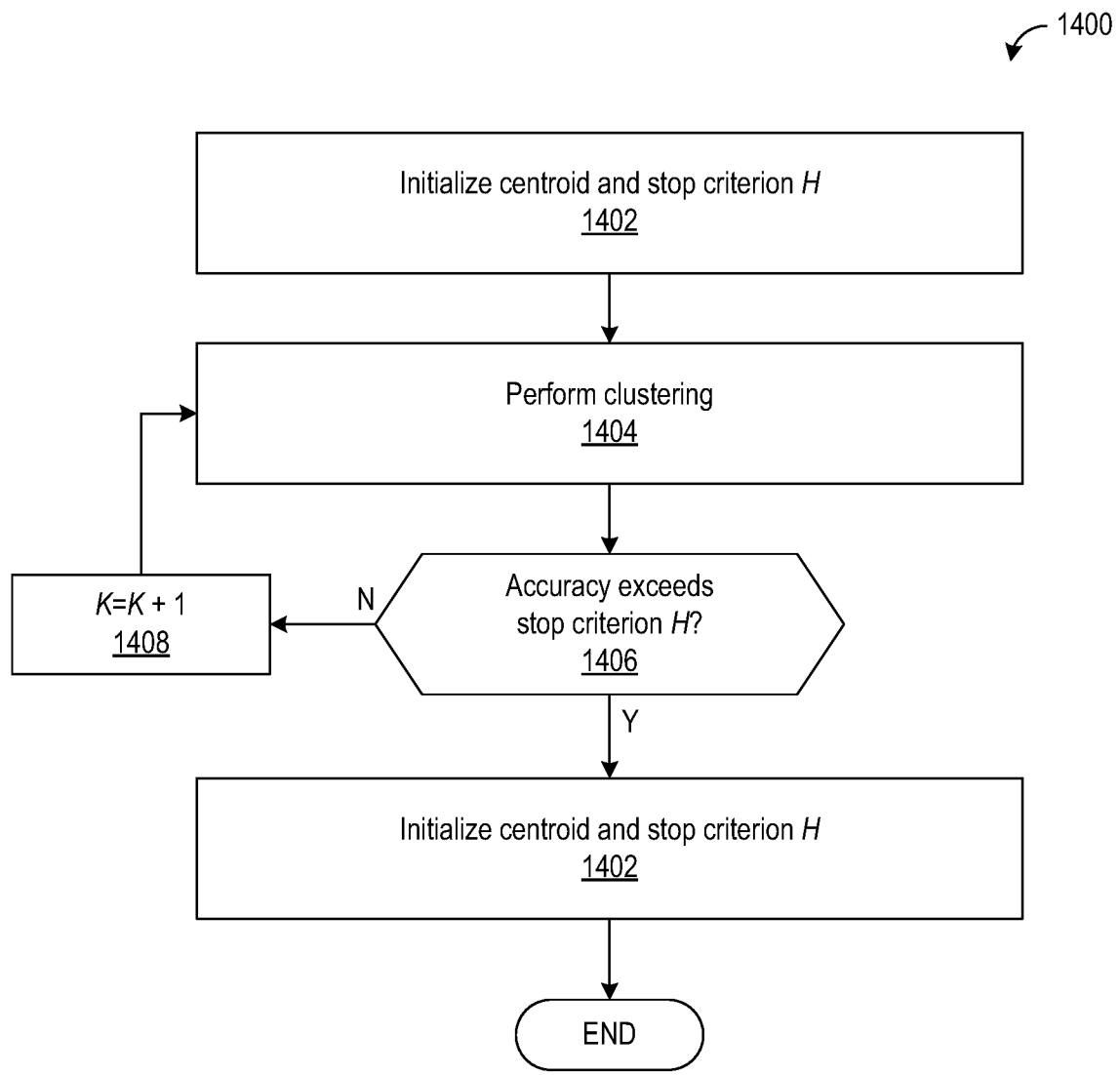
FIGS. 14A and 14B illustrate a method of training a multi-centroid classifier.
Figure 14B:
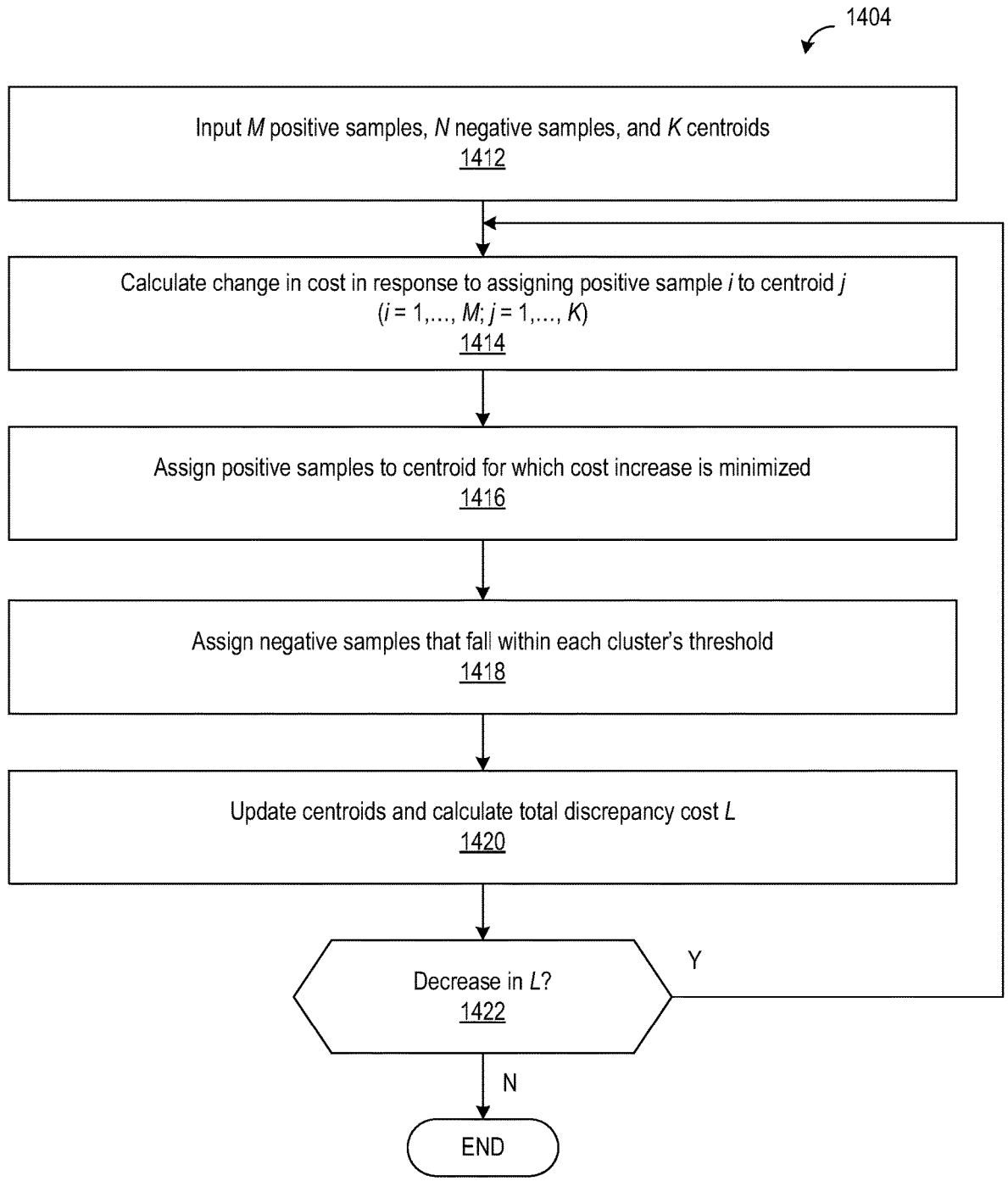

FIGS. 14A and 14B illustrate an example method 1400 of training a multi-centroid classifier. Method 1400 can be performed by a device including a health event determining system as described herein (collectively "the system").

At block 1402, the system initializes a centroid and a predetermined stop criterion H. The centroid can be randomly chosen. At block 1404, the system performs clustering by successively adding clusters with the objective of achieving an accuracy that exceeds the predetermined stop criterion H, subject to the constraints shown in FIG. 14B. If at decision block 1406, the accuracy of the clustering of the examples does not exceed stop criterion H, then at block 1408 the K+1 cluster is added to an existing K clusters. Otherwise, if the accuracy of the multi-centroid classifier classifies the example samples with accuracy that exceeds stop criterion H, then the system at block 1410 outputs the centroids and their corresponding thresholds for use in classifying motion signals (real-time samples).

FIG. 14B provides greater detail of system clustering 1404. At block 1412, the system receives as examples for training the multi-centroid classifier M positive samples and N negative samples. Positive samples comprise motion events (motion signal segments) of interest—that is, an individual's movement that correspond to a health event. Negative samples comprise motion events that do not correspond to a health event and thus are not sound events of interest. At block 1414, the system calculates the change in cost (defined above) from assigning the i-th positive sample to the j-th centroid (template). Based on the calculation, system assigns the i-th positive sample to the centroid that incurs the smallest cost increase. At block 1418, the system assigns each negative sample to the cluster within whose boundary it falls—that is, to the cluster for which a distance between negative sample and centroid is less than the cluster's threshold. At block 1420, the system then updates the centroids and calculates the total discrepancy cost, L (defined above). As long as adding another cluster and assigning positive and negative samples decreases discrepancy cost L at decision block 1422, the system continues the process. If adding a cluster fails to decrease discrepancy cost L, then the iterative process of clustering 1404 ends.

Various arrangements of multilayered health event detection and identification have been described. In each arrangement, a potential occurrence of a predetermined health event is detected based on template matching—using, for example, the novel multi-centroid classifier—applied to motion signals generated by the motion of a device user. Illustratively, the arrangements have involved analyzing audio signals using a multilayered audio event classifier. Processing audio signals is invoked in response to detecting the potential occurrence of the predetermined health event based on the real-time processing of motion signals using template matching. In various other arrangements, other types of signal processing can be performed in response to detecting a potential occurrence of a predetermined health event based on template matching.

For example, in certain arrangements, a photoplethysmography (PPG) sensor can be used to monitor cardiac functions of the device user. The operation of the PPG sensor is invoked in response to detecting, based on template matching of motion sensor-generated signals, a device user's fall or other motion corresponding to a potential occurrence of a predetermined health event such as heart arrhythmia or cardiac arrest. In other arrangements, other types of signal processing can be performed. In each such arrangement, processing signals generated by one or more sensors is invoked in response to detecting a potential occurrence of a predetermined health event based on template matching applied with respect to motion signals. Unless and until a predetermined health event is detected based on template matching of motion signals no other processing is performed. Limiting the signal processing enhances the efficient use of processors, memory, and power of the device, enabling use in a resource-limited device such as a portable device or wearable (e.g., earbuds).

FIG. 15 illustrates an example device 1500 configured for operation as a system. Device 1500 includes one or more processors 1502 coupled to memory 1504 through interface circuitry 1506. Device 1500 stores computer readable instructions (also referred to as "program code") within memory 1504, which is an example of computer readable storage media. Processor(s) 1506 execute the program code accessed from memory 1504 via interface circuitry 1506.

Memory 1504 can include one or more physical memory devices such as local memory 1508 and bulk storage device 1510, for example. Local memory 1508 is implemented as one or more non-persistent memory device(s) generally used during actual execution of the program code. Local memory 1508 is an example of a runtime memory. Examples of local memory 1508 include any of the various types of RAM suitable for use by a processor for executing program code. Bulk storage device 1510 is implemented as a persistent data storage device. Examples of bulk storage device 1510 include a hard disk drive (HDD), a solid-state drive (SSD), flash memory, a read-only memory (ROM), an erasable programmable read-only memory (EPROM), electrically erasable programmable read-only memory (EEPROM), or other suitable memory. Device 1500 can also include one or more cache memories (not shown) that provide temporary storage of at least some program code in order to reduce the number of times program code must be retrieved from a bulk storage device during execution.

Examples of interface circuitry 1506 include, but are not limited to, an input/output (I/O) subsystem, an I/O interface, a bus system, and a memory interface. For example, interface circuitry 1506 can be implemented as any of a variety of bus structures and/or combinations of bus structures including a memory bus or memory controller, a peripheral bus, an accelerated graphics port, and a processor or local bus.

In one or more example implementations, processor(s) 1502, memory 1504, and/or interface circuitry 1506 are implemented as separate components. Processor(s) 1502, memory 1504, and/or interface circuitry 1506 may be integrated in one or more integrated circuits. The various components in device 1500, for example, can be coupled by one or more communication buses or signal lines (e.g., interconnects and/or wires). Memory 1504 may be coupled to interface circuitry 1506 via a memory interface, such as a memory controller or other memory interface (not shown).

Although not feasible if device 1500 is a wearable such as a pair of earbuds, if device 1500 is another type such as a smartphone or smartwatch, device 1500 can include one or more displays. Illustratively, for example, device 1500 includes display 1512 (e.g., a screen). Display 1512 can be implemented as a touch-sensitive or touchscreen display capable of receiving touch input from a user. A touch sensitive display and/or a touch-sensitive pad is capable of detecting contact, movement, gestures, and breaks in contact using any of a variety of available touch sensitivity technologies. Example touch sensitive technologies include, but are not limited to, capacitive, resistive, infrared, and surface acoustic wave technologies, and other proximity sensor arrays or other elements for determining one or more points of contact with a touch sensitive di splay and/or device.

Likewise, if device 1500 is a device such as smartphone rather than a pair of earbuds, then device 1500 can include multimedia sensors such as camera subsystem 1514. Camera subsystem 1514 can be coupled to interface circuitry 1506 directly or through a suitable input/output (I/O) controller. Camera subsystem 1514 can be coupled to optical sensor 1516. Optical sensor 1516 can be implemented using any of a variety of technologies. Examples of optical sensor 1516 can include, but are not limited to, a charged coupled device (CCD) or a complementary metal-oxide semiconductor (CMOS) optical sensor. Optical sensor 1516, for example, can be a depth sensor. Camera subsystem 1514 and optical sensor 1516 are capable of performing camera functions such as recording or capturing images and/or recording video.

Device 1500 can include other multimedia sensors such as an audio subsystem 1518. Audio subsystem 1518 can be coupled to interface circuitry 1506 directly or through a suitable input/output (I/O) controller. Audio subsystem 1518 can be coupled to a speaker 1520 and a microphone 1522 to facilitate voice-enabled functions, such as voice recognition, voice replication, digital recording, and telephony functions.

Device 1500 can include one or more wireless communication subsystems 1524. Each of wireless communication subsystem(s) 1524 can be coupled to interface circuitry 1506 directly or through a suitable I/O controller (not shown). Each of wireless communication subsystem(s) 1524 is capable of facilitating communication functions. Examples of wireless communication subsystems 1524 can include, but are not limited to, radio frequency receivers and transmitters, and optical (e.g., infrared) receivers and transmitters. The specific design and implementation of wireless communication subsystem 1524 can depend on the particular type of device 1500 implemented and/or the communication network(s) over which device 1500 is intended to operate.

As an illustrative and non-limiting example, wireless communication subsystem(s) 1524 may be designed to operate over one or more mobile networks, WiFi networks, short range wireless networks (e.g., a Bluetooth), and/or any combination of the foregoing. Wireless communication subsystem(s) 1524 can implement hosting protocols such that device 1500 can be configured as a base station for other wireless devices.

Device 1500 may include one or more sensors 1526, each of which can be coupled to interface circuitry 1506 directly or through a suitable I/O controller (not shown). Sensor(s) 1526 can include various types of sensors. Sensor(s) 1526 can include a sound transducer and/or other audio sensor(s). Sensor(s) 1526 can include one or more motion sensors. The motion sensor(s) can include one or more multi-axis IMUs. The IMU(s) can combine a micro-electro-mechanical system (MEMS) accelerometer and a MEMS gyroscope. Other examples of sensors 1526 can include, but are not limited to, a location sensor (e.g., a GPS receiver and/or processor) capable of providing geo-positioning sensor data, an electronic magnetometer (e.g., an integrated circuit chip) capable of providing sensor data that can be used to determine the direction of magnetic North for purposes of directional navigation, an accelerometer capable of providing data indicating change of speed and direction of movement of device 1500 and an altimeter (e.g., an integrated circuit) capable of providing data indicating altitude. Sensor(s) 1526 can include Device 1500 further may include one or more input/output (I/O) devices 1528 coupled to interface circuitry 1506. I/O device(s) 1528 can be coupled to interface circuitry 1506 either directly or through intervening I/O controllers (not shown). Examples of I/O devices 1528 include, but are not limited to, a track pad, a keyboard, a display device, a pointing device, one or more communication ports (e.g., Universal Serial Bus (USB) ports), a network adapter, and buttons or other physical controls. A network adapter refers to circuitry that enables device 1500 to become coupled to other systems, computer systems, remote printers, and/or remote storage devices through intervening private or public networks. Modems, cable modems, Ethernet interfaces, and wireless transceivers not part of wireless communication subsystem(s) 1524 are examples of different types of network adapters that may be used with device 1500. One or more of I/O devices 1528 may be adapted to control functions of one or more or all of sensors 1526 and/or one or more of wireless communication subsystem(s) 1524.

Memory 1504 stores program code. Examples of program code include, but are not limited to, routines, programs, objects, components, logic, and other data structures. For purposes of illustration, memory 1504 stores an operating system 1530 and application(s) 1532. In addition, memory 1504 can include health event determination program code 1534 and multi-centroid classifier program code 1536 for implementing a health event determining system, optionally including a multi-centroid classifier, such as system 100 (FIG. 1).

Device 1500 is provided for purposes of illustration and not limitation. A device and/or system configured to perform the operations described herein can have a different architecture than illustrated in FIG. 15. The architecture can be a simplified version of the architecture described in connection with FIG. 15 that includes a memory capable of storing instructions and a processor capable of executing instructions. In this regard, device 1500 may include fewer components than shown or additional components not illustrated in FIG. 15 depending upon the particular type of device that is implemented. In addition, the particular operating system and/or application(s) included can vary according to device type as can the types of I/O devices included. Further, one or more of the illustrative components can be incorporated into, or otherwise form a portion of, another component. For example, a processor may include at least some memory.

Device 1500 can be implemented as a data processing system, a communication device, or other suitable system that is suitable for storing and/or executing program code. Device 1500 can be implemented as an edge device. Example implementations of device 1500 can include, but are not to limited to, earbuds, a smartwatch, a pair of smart glasses, an HMD device, or other wearable device, a smartphone or other portable device, laptop, tablet, or other computing device.

The terminology used herein is for the purpose of describing particular embodiments only and is not intended to be limiting. Notwithstanding, several definitions that apply throughout this document are expressly defined as follows.

As defined herein, the singular forms "a," "an," and "the" are intended to include the plural forms as well, unless the context clearly indicates otherwise.

The term "approximately" means nearly correct or exact, close in value or amount but not precise. For example, the term "approximately" may mean that the recited characteristic, parameter, or value is within a predetermined amount of the exact characteristic, parameter, or value.

As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without human intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. The different types of memory, as described herein, are examples of a computer readable storage media. A non-exhaustive list of more specific examples of a computer readable storage medium may include: a portable computer diskette, a hard disk, a random-access memory (RAM), a read-only memory (ROM), an erasable programmable read-only memory (EPROM or Flash memory), a static random-access memory (SRAM), a portable compact disc read-only memory (CD-ROM), a digital versatile disk (DVD), a memory stick, a floppy disk, or the like.

As defined herein, "data processing system" means one or more hardware systems configured to process data, each hardware system including at least one processor programmed to initiate operations and memory.

As defined herein, "execute" and "run" comprise a series of actions or events performed by the processor in accordance with one or more machine-readable instructions. "Running" and "executing," as defined herein refer to the active performing of actions or events by the processor. The terms run, running, execute, and executing are used synonymously herein.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the terms "individual" and "user" refer to a human being.

As defined herein, the term "processor" means at least one hardware circuit. The hardware circuit may be configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "responsive to" and similar language as described above, (e.g., "if," "when," or "upon,") mean responding or reacting readily to an action or event. The response or reaction is performed automatically. Thus, if a second action is performed "responsive to" a first action, there is a causal relationship between an occurrence of the first action and an occurrence of the second action. The term "responsive to" indicates the causal relationship.

As defined herein, "real-time" means a level of processing responsiveness that a user or system senses as sufficiently immediate for a particular process or determination to be made, or that enables the processor to keep up with some external process. Relatedly, "real-time processing" means processing activity carried out in real time.

As defined herein, "server" means a data processing system configured to share services with one or more other data processing systems. Relatedly, "client device" means a data processing system that requests shared services from a server, and with which a user directly interacts. Examples of a client device include, but are not limited to, a workstation, a desktop computer, a computer terminal, a mobile computer, a laptop computer, a netbook computer, a tablet computer, a smart phone, a personal digital assistant, a smart watch, smart glasses, a gaming device, a set-top box, a smart television, and the like. In one or more embodiments, the various user devices described herein may be client devices. Network infrastructure, such as routers, firewalls, switches, access points and the like, are not client devices as the term "client device" is defined herein.

As defined herein, "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object-oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions (e.g., program code).

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various aspects of the inventive arrangements. In this regard, each block in the flowcharts or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method, comprising:
   detecting, using a user device, a potential occurrence of a predetermined health event for a user by processing in real-time motion signals corresponding to motion of the user;
   determining a likelihood that the potential occurrence is an actual occurrence of the predetermined health event based on template matching of the motion signals; and
   in response to determining that the likelihood exceeds a predetermined threshold, processing audio signals coinciding in time with the motion of the user using one or more layers of a multilayered audio event classifier.

2. The method of claim 1, wherein
   the template matching is performed using a self-tuning multi-centroid classifier.

3. The method of claim 1, wherein
   the processing the audio signals includes:
      in response to detecting, at a first layer of the multilayered audio event classifier, audio signals corresponding to voice activity, filtering the audio signals to separate the audio signals corresponding to voice activity from audio signals corresponding to non-voice activity;
      in response to detecting, at a second layer of the multilayered audio event classifier, one or more sharp sound events within the audio signals corresponding to voice activity, processing the audio signals corresponding to voice activity to separate the one or more sharp sound events contained therein from non-sharp sound events; and
      classifying the sharp sound events using a machine learning classifier.

4. The method of claim 3, further comprising:
selecting one of a plurality of machine learning classifiers for classifying the sharp sound events, wherein the selecting is based on determining an availability of resources of the device.

5. The method of claim 1, further comprising:
conveying the audio signals to an auxiliary device communicatively coupled with the device, wherein the processing the audio signals with a multilayered audio event classifier is performed by the auxiliary device.

6. The method of claim 5, wherein
the conveying the audio signals is performed in response to detecting that a power level of the device is less than a predetermined threshold.

7. The method of claim 5, wherein
the device is a wearable device, and the auxiliary device comprises a plurality of auxiliary devices, and wherein the method further comprises:
  detecting that the wearable device is positioned to impede generating at least one of the motion signals or the audio signals using one or more sensors of the wearable device; and
  automatically selecting one of the plurality of auxiliary devices for generating the at least one of the motion signals or the audio signals.

8. The method of claim 1, further comprising:
detecting at least one of acoustic noise or motion noise above a predetermined threshold within a selected segment of at least one of the motion signals or the audio signals; and
discarding the selected segment.

9. The method of claim 1, wherein
the actual health event is a pulmonary event, and wherein the method further comprises:
  performing a lung function parameter estimation in response to the pulmonary event.

10. The method of claim 9, further comprising:
performing an orientation calibration that includes at least one of generating a user-specific template for retraining a model used for the template matching or generating a transfer function based on a user-specific baseline for calibrating a motion sensor for sensing the real-time motion signals.

11. A system, comprising:
one or more processors configured to initiate operations including:
  detecting a potential occurrence of a predetermined health event for a user by processing in real-time motion signals corresponding to motion of the user;
  determining a likelihood that the potential occurrence is an actual occurrence of the predetermined health event based on template matching of the motion signals; and
  in response to determining that the likelihood exceeds a predetermined threshold, processing audio signals coinciding in time with the motion of the user using one or more layers of a multilayered audio event classifier.

12. The system of claim 11, wherein
the template matching is performed using a self-tuning multi-centroid classifier.

13. The system of claim 11, wherein
the processing the audio signals includes:
  in response to detecting, at a first layer of the multilayered audio event classifier, audio signals corresponding to voice activity, filtering the audio signals to separate the audio signals corresponding to voice activity from audio signals corresponding to non-voice activity;
  in response to detecting, at a second layer of the multilayered audio event classifier, one or more sharp sound events within the audio signals corresponding to voice activity, processing the audio signals corresponding to voice activity to separate the one or more sharp sound events contained therein from non-sharp sound events; and
  classifying the sharp sound events using a machine learning classifier.

14. The system of claim 13, wherein the processor is configured to initiate operations further including:
selecting one of a plurality of machine learning classifiers for classifying the sharp sound events, wherein the selecting is based on determining an availability of resources of a device in which the system is implemented.

15. The system of claim 11, wherein the processor is configured to initiate operations further including:
conveying the audio signals from a device in which the system is implemented to an auxiliary device communicatively coupled with the device, wherein the processing the audio signals with a multilayered audio event classifier is performed by the auxiliary device.

16. The system of claim 15, wherein
the conveying the audio signals is performed in response to detecting that a power level of the device is less than a predetermined threshold.

17. The system of claim 15, wherein
the device is a wearable device, and the auxiliary device comprises a plurality of auxiliary devices, and wherein the processor is configured to initiate operations further including:
  detecting that the wearable device is positioned to impede generating at least one of the motion signals or the audio signals using one or more sensors of the wearable device; and
  automatically selecting one of the plurality of auxiliary devices for generating the at least one of the motion signals or the audio signals.

18. The system of claim 11, wherein the processor is configured to initiate operations further including:
  detecting at least one of acoustic noise or motion noise above a predetermined threshold within a selected segment of at least one of the motion signals or the audio signals; and
  discarding the selected segment.

19. The system of claim 11, wherein
the actual health event is a pulmonary event, and wherein the processor is configured to initiate operations further including:
  performing a lung function parameter estimation in response to the pulmonary event.

20. A computer program product, the computer program product comprising:
one or more computer-readable storage media and program instructions collectively stored on the one or more computer-readable storage media, the program instructions executable by a processor to cause the processor to initiate operations including:
  detecting a potential occurrence of a predetermined health event for a user by processing in real-time motion signals corresponding to motion of the user;

determining a likelihood that the potential occurrence is an actual occurrence of the predetermined health event based on template matching of the motion signals; and in response to determining that the likelihood exceeds a predetermined threshold, processing audio signals coinciding in time with the motion of the user using one or more layers of a multilayered audio event classifier.

\* \* \* \* \*